(12) United States Patent
Toth

(10) Patent No.: US 10,828,220 B2
(45) Date of Patent: Nov. 10, 2020

(54) DEVICE, SYSTEM AND METHOD FOR COMPRESSION TREATMENT OF A BODY PART

(71) Applicant: Swelling Solutions, Inc., Minneapolis, MN (US)

(72) Inventor: Landy Toth, Newtown, PA (US)

(73) Assignee: Tactile Systems Technology Inc., Minneapolis, MN (US)

( * ) Notice: Subject to any disclaimer, the term of this patent is extended or adjusted under 35 U.S.C. 154(b) by 1171 days.

(21) Appl. No.: 15/008,917

(22) Filed: Jan. 28, 2016

(65) Prior Publication Data

US 2016/0193100 A1 Jul. 7, 2016

Related U.S. Application Data

(63) Continuation of application No. 14/299,201, filed on Jun. 9, 2014, now Pat. No. 9,248,074, which is a
(Continued)

(51) Int. Cl.
*A61H 1/00* (2006.01)
*A61H 11/00* (2006.01)
(Continued)

(52) U.S. Cl.
CPC .......... *A61H 1/008* (2013.01); *A61F 13/085* (2013.01); *A61H 11/00* (2013.01);
(Continued)

(58) Field of Classification Search
CPC .............. A61H 11/00–02; A61H 31/00; A61H 31/004–006; A61H 2201/0192–0196; A61H 2201/12–123; A61H 2201/14; A61H 2201/1418; A61H 2201/1481–149; A61H 2201/5061; A61H 2209/00; A61B 17/132–1325; A61F 2013/0028
See application file for complete search history.

(56) References Cited

U.S. PATENT DOCUMENTS 3,826,249 A 7/1974 Lee et al.
4,013,069 A 3/1977 Hasty
(Continued)

FOREIGN PATENT DOCUMENTS

DE 10 2010 021 902 A1 12/2011
EP 0 210 002 A1 1/1987
(Continued)

OTHER PUBLICATIONS

Bar-Cohen, "Electroactive Polymer (EAP) Actuators as Artificial Muscles: Reality, Potential, and Challengs," 2$^{nd}$ Ed., Chapter 1, SPIE Press, Bellingham; 2004.
(Continued)

*Primary Examiner* — Rachel T Sippel
(74) *Attorney, Agent, or Firm* — Mueting Raasch Group

(57) ABSTRACT

A device for compressive treatment of a body part includes a compression member, adapted to at least partly encircle the body part, and an actuation unit, arranged to tighten the compression member to provide a compressive force to the body part. Methods are provided for its therapeutic, cosmetic and non-therapeutic use and operation.

17 Claims, 20 Drawing Sheets

Related U.S. Application Data continuation of application No. 12/160,674, filed as application No. PCT/EP2006/000276 on Jan. 13, 2006, now Pat. No. 8,764,689.

(51) Int. Cl.
  *A61H 23/02* (2006.01)
  *A61F 13/08* (2006.01)

(52) U.S. Cl.
  CPC .... *A61H 23/0254* (2013.01); *A61H 2011/005* (2013.01); *A61H 2201/0111* (2013.01); *A61H 2201/1207* (2013.01); *A61H 2201/1215* (2013.01); *A61H 2201/149* (2013.01); *A61H 2201/1642* (2013.01); *A61H 2201/1654* (2013.01); *A61H 2201/1688* (2013.01); *A61H 2201/1695* (2013.01); *A61H 2201/1697* (2013.01); *A61H 2201/5061* (2013.01); *A61H 2201/5071* (2013.01); *A61H 2205/10* (2013.01); *A61H 2209/00* (2013.01); *A61H 2230/30* (2013.01)

(56) References Cited

U.S. PATENT DOCUMENTS

| | | |
|---|---|---|
| 4,029,087 A | 6/1977 | Dye et al. |
| 4,030,488 A | 6/1977 | Hasty |
| 4,054,540 A | 10/1977 | Michalchik |
| 4,091,804 A | 5/1978 | Hasty |
| 4,207,876 A | 6/1980 | Annis |
| 4,256,094 A | 3/1981 | Kapp |
| 4,269,175 A | 5/1981 | Dillon |
| 4,292,261 A | 9/1981 | Kotani et al. |
| 4,320,746 A | 3/1982 | Arkans |
| 4,374,518 A | 2/1983 | Villanueva |
| 4,396,010 A | 8/1983 | Arkans |
| 4,402,312 A | 9/1983 | Villari |
| 4,408,599 A | 10/1983 | Nummert |
| 4,573,453 A | 3/1986 | Tissot et al. |
| 4,762,121 A | 8/1988 | Shienfeld |
| 4,996,511 A | 2/1991 | Ohkawa et al. |
| 5,007,411 A | 4/1991 | Dye |
| 5,014,681 A | 5/1991 | Neeman |
| 5,022,387 A | 6/1991 | Hasty |
| 5,031,604 A | 7/1991 | Dye |
| 5,052,377 A | 10/1991 | Frajdenrajch et al. |
| 5,108,455 A | 4/1992 | Telikicherla |
| 5,113,887 A | 5/1992 | Herman, Jr. |
| 5,117,812 A | 6/1992 | McWhorter |
| 5,172,689 A | 12/1992 | Wright |
| 5,175,214 A | 12/1992 | Takaya et al. |
| 5,179,941 A | 1/1993 | Siemssen |
| 5,186,163 A | 2/1993 | Dye |
| 5,193,549 A | 3/1993 | Bellin |
| 5,263,473 A | 11/1993 | McWhorter |
| 5,302,936 A | 4/1994 | Yaniger |
| 5,324,317 A | 6/1994 | Reiss |
| 5,370,133 A | 12/1994 | Darby |
| 5,372,575 A | 12/1994 | Sebastian |
| 5,374,283 A | 12/1994 | Flick |
| 5,383,894 A | 1/1995 | Dye |
| 5,437,610 A | 8/1995 | Cariapa |
| 5,443,440 A | 8/1995 | Tumey |
| 5,452,878 A | 9/1995 | Gravesen et al. |
| 5,453,081 A | 9/1995 | Hansen |
| 5,453,653 A | 9/1995 | Zumeris |
| 5,575,762 A | 11/1996 | Peeler |
| 5,583,303 A | 12/1996 | Franz |
| 5,591,200 A | 1/1997 | Cone |
| 5,596,241 A | 1/1997 | Seki et al. |
| 5,626,556 A | 5/1997 | Tobler |
| 5,643,331 A | 7/1997 | Katz |
| 5,653,244 A | 8/1997 | Shaw et al. |
| 5,725,581 A | 3/1998 | Branemark |
| 5,759,164 A | 6/1998 | Pacey |
| 5,795,312 A | 8/1998 | Dye |
| 5,843,007 A | 12/1998 | McEwen et al. |
| 5,876,359 A | 3/1999 | Bock et al. |
| 5,897,517 A | 4/1999 | Laghi |
| 5,904,145 A | 5/1999 | Reid |
| 5,906,206 A | 5/1999 | Shaw et al. |
| 5,916,183 A | 6/1999 | Reid |
| 5,918,602 A | 7/1999 | Shaw et al. |
| 5,951,502 A | 9/1999 | Peeler et al. |
| 5,957,867 A | 9/1999 | Lloyd |
| 5,997,465 A | 12/1999 | Savage |
| 6,007,559 A | 12/1999 | Arkans |
| 6,010,471 A | 1/2000 | Ben-Noon |
| 6,041,243 A | 3/2000 | Davidson et al. |
| 6,062,244 A | 5/2000 | Arkans |
| 6,076,013 A | 6/2000 | Brennan et al. |
| 6,109,267 A | 8/2000 | Shaw et al. |
| 6,121,870 A | 9/2000 | Ariga et al. |
| 6,123,681 A | 9/2000 | Brown |
| 6,179,796 B1 | 1/2001 | Waldridge |
| 6,196,231 B1 | 3/2001 | Reid |
| 6,198,204 B1 | 3/2001 | Pottenger |
| 6,231,532 B1 | 5/2001 | Watson |
| 6,254,554 B1 | 7/2001 | Turtzo |
| 6,267,744 B1 | 7/2001 | Roberts |
| 6,282,448 B1 | 8/2001 | Katz |
| 6,290,662 B1 | 9/2001 | Morris et al. |
| 6,291,568 B1 | 9/2001 | Lussey |
| 6,296,617 B1 | 10/2001 | Peeler et al. |
| 6,315,745 B1 | 11/2001 | Kloecker |
| 6,332,091 B1 | 12/2001 | Burns et al. |
| 6,338,723 B1 | 1/2002 | Carpenter et al. |
| 6,355,008 B1 | 3/2002 | Nakao |
| 6,388,556 B1 | 5/2002 | Imai et al. |
| 6,436,064 B1 | 8/2002 | Kloecker |
| 6,436,448 B1 | 8/2002 | Yue |
| 6,437,485 B1 | 8/2002 | Johansson |
| 6,440,093 B1 | 8/2002 | McEwen et al. |
| 6,463,934 B1 | 10/2002 | Johnson, Jr. et al. |
| 6,488,677 B1 | 12/2002 | Bowman et al. |
| 6,491,652 B1 | 12/2002 | Hata |
| 6,494,852 B1 | 12/2002 | Barak |
| 6,506,206 B1 | 1/2003 | Guzman et al. |
| 6,544,202 B2 | 4/2003 | McEwen et al. |
| 6,558,338 B1 | 5/2003 | Wasserman |
| 6,613,350 B1 | 9/2003 | Zhang et al. |
| 6,616,620 B2 * | 9/2003 | Sherman .............. A61H 31/00 601/41 |
| 6,620,116 B2 | 9/2003 | Lewis |
| 6,645,165 B2 | 11/2003 | Waldridge et al. |
| 6,656,141 B1 | 12/2003 | Reid |
| 6,714,019 B2 | 3/2004 | Kirbayashi et al. |
| 6,749,556 B2 | 6/2004 | Banik |
| 6,765,335 B2 | 7/2004 | Wischnewskiy |
| 6,846,295 B1 | 1/2005 | Ben-Nun |
| 6,860,862 B2 | 3/2005 | Waldridge et al. |
| 6,870,304 B2 | 3/2005 | Magnussen |
| 6,960,159 B2 | 11/2005 | Chung et al. |
| 6,966,884 B2 | 11/2005 | Waldridge et al. |
| 6,979,333 B2 | 12/2005 | Hammerslag |
| 6,988,423 B2 | 1/2006 | Bolam et al. |
| 7,001,384 B2 | 2/2006 | Berish et al. |
| 7,022,093 B2 | 4/2006 | Smith et al. |
| 7,044,924 B1 | 5/2006 | Roth et al. |
| 7,056,297 B2 | 6/2006 | Dohno et al. |
| 7,074,200 B1 | 7/2006 | Lewis |
| 7,080,562 B2 | 7/2006 | Knowles et al. |
| 7,214,847 B1 | 5/2007 | Flick |
| 7,257,051 B2 | 8/2007 | Thoemius et al. |
| 7,327,637 B2 | 2/2008 | Chambers et al. |
| 7,329,232 B2 | 2/2008 | Lipshaw et al. |
| 7,354,410 B2 | 4/2008 | Perry et al. |
| 7,442,175 B2 | 10/2008 | Meyer et al. |
| 7,481,782 B2 | 1/2009 | Scott et al. |
| 7,491,185 B2 | 2/2009 | Couvillon, Jr. |
| 7,548,015 B2 | 6/2009 | Benslimane et al. |
| 7,569,974 B2 | 8/2009 | D'Almeida et al. |
| 7,573,064 B2 | 8/2009 | Benslimane et al. |

(56) References Cited

U.S. PATENT DOCUMENTS

| | | |
|---|---|---|
| 7,591,050 B2 | 9/2009 | Hammerslag |
| 7,618,384 B2 | 11/2009 | Nardi et al. |
| 7,637,879 B2 | 12/2009 | Barak et al. |
| 7,637,922 B2 | 12/2009 | Johnson et al. |
| 7,732,999 B2 | 6/2010 | Clausen et al. |
| 7,785,905 B2 | 8/2010 | Benslimane |
| 7,857,777 B2 | 12/2010 | Larson et al. |
| 7,868,221 B2 | 1/2011 | Munch-Fals et al. |
| 7,880,371 B2 | 2/2011 | Benslimane et al. |
| 7,895,728 B2 | 3/2011 | Benslimane et al. |
| 7,976,924 B2 | 7/2011 | Stanford, Jr. et al. |
| 7,992,217 B2 | 8/2011 | Hyde et al. |
| 8,029,451 B2 | 10/2011 | Meyer et al. |
| 8,079,969 B2 | 12/2011 | Rousso et al. |
| 8,079,970 B2 | 12/2011 | Meyer et al. |
| 8,083,644 B2 | 12/2011 | Purdy et al. |
| 8,100,841 B2 | 1/2012 | Rousso |
| 8,100,842 B2 | 1/2012 | Rousso |
| 8,105,252 B2 | 1/2012 | Rousso |
| 8,257,289 B2 | 9/2012 | Vess |
| 8,381,362 B2 | 2/2013 | Hammerslag et al. |
| 8,388,557 B2 | 3/2013 | Moomiaie-Qajar et al. |
| 8,394,042 B1 | 3/2013 | Mirza |
| 8,491,514 B2 | 7/2013 | Creighton et al. |
| 8,578,939 B1 | 11/2013 | Kimani Mwangi et al. |
| 8,764,689 B2 | 7/2014 | Toth |
| 9,248,074 B2 | 2/2016 | Toth |
| 2001/0002840 A1 | 6/2001 | Casserino et al. |
| 2002/0074901 A1 | 6/2002 | Johansson |
| 2002/0091344 A1 | 7/2002 | Thomas et al. |
| 2002/0173735 A1 | 11/2002 | Lewis |
| 2003/0004445 A1* | 1/2003 | Hall .......... A61H 9/0078 601/41 |
| 2003/0176825 A1 | 9/2003 | Yavnai |
| 2003/0212306 A1 | 11/2003 | Banik |
| 2004/0073146 A1 | 4/2004 | Weintraub |
| 2004/0167365 A1 | 8/2004 | Chuang |
| 2004/0181179 A1 | 9/2004 | Hwang |
| 2005/0043657 A1 | 2/2005 | Couvillon, Jr. |
| 2005/0159690 A1 | 7/2005 | Barak et al. |
| 2005/0187503 A1 | 8/2005 | Tordella et al. |
| 2006/0074362 A1 | 4/2006 | Rousso et al. |
| 2006/0111655 A1 | 5/2006 | Cook et al. |
| 2006/0156517 A1 | 7/2006 | Hammerslag et al. |
| 2006/0258964 A1 | 11/2006 | Biondo et al. |
| 2006/0287672 A1 | 12/2006 | McEwen et al. |
| 2007/0029197 A1 | 2/2007 | DiFoggio et al. |
| 2007/0169378 A1 | 7/2007 | Sodeberg et al. |
| 2008/0039752 A1 | 2/2008 | Rousso |
| 2008/0188782 A1 | 8/2008 | Carkner et al. |
| 2008/0195018 A1 | 8/2008 | Larson et al. |
| 2008/0255494 A1 | 10/2008 | Rousso et al. |
| 2009/0018474 A1 | 1/2009 | Nakao |
| 2009/0064476 A1 | 3/2009 | Cross et al. |
| 2009/0118651 A1 | 5/2009 | Rousso et al. |
| 2009/0234265 A1 | 9/2009 | Reid, Jr. et al. |
| 2009/0299249 A1 | 12/2009 | Wilkes et al. |
| 2010/0010404 A1 | 1/2010 | Nardi et al. |
| 2010/0010406 A1 | 1/2010 | Nardi et al. |
| 2010/0036299 A1 | 2/2010 | Gough |
| 2010/0056966 A1 | 3/2010 | Toth |
| 2010/0204803 A1 | 8/2010 | Tozzi et al. |
| 2010/0228171 A1 | 9/2010 | Waldridge |
| 2010/0305484 A1 | 12/2010 | Grollier et al. |
| 2011/0009795 A1 | 1/2011 | Graham et al. |
| 2011/0066093 A1 | 3/2011 | Vess |
| 2011/0082401 A1 | 4/2011 | Iker et al. |
| 2011/0119812 A1 | 5/2011 | Genz et al. |
| 2011/0125183 A1 | 5/2011 | Lipshaw et al. |
| 2011/0131839 A1 | 6/2011 | Ballin et al. |
| 2011/0156530 A1 | 6/2011 | Yamamoto et al. |
| 2011/0162200 A1 | 7/2011 | Benslimane et al. |
| 2011/0196269 A1 | 8/2011 | Arkans |
| 2011/0245743 A1 | 10/2011 | Eddy |
| 2012/0004587 A1 | 1/2012 | Nickel et al. |
| 2013/0012856 A1 | 1/2013 | Hammerslag et al. |
| 2013/0184622 A1 | 7/2013 | Farrow |
| 2013/0269219 A1 | 10/2013 | Burns et al. |
| 2013/0283500 A1 | 10/2013 | Lipshaw et al. |
| 2013/0345610 A1 | 12/2013 | Larson et al. |
| 2014/0094728 A1 | 4/2014 | Soderberg et al. |
| 2014/0123440 A1 | 5/2014 | Capra et al. |
| 2014/0123449 A1 | 5/2014 | Soderberg et al. |

FOREIGN PATENT DOCUMENTS

| | | |
|---|---|---|
| EP | 0 329 470 A2 | 8/1989 |
| EP | 0 475 752 A2 | 3/1992 |
| EP | 1 018 329 B1 | 7/2000 |
| EP | 1 324 403 A1 | 2/2003 |
| EP | 1 324 406 A2 | 2/2003 |
| EP | 1 533 678 A1 | 11/2003 |
| EP | 1 596 794 B1 | 11/2005 |
| EP | 1 645 254 A1 | 4/2006 |
| JP | 1999/009633 | 6/1997 |
| JP | 2002/336320 | 5/2001 |
| JP | 2003/062023 | 8/2001 |
| SU | 1245312 A1 | 7/1986 |
| WO | WO 02/45697 A2 | 6/2002 |
| WO | WO 02/055005 A1 | 7/2002 |
| WO | WO 03/105946 A1 | 12/2003 |
| WO | WO 2004/084790 A1 | 10/2004 |
| WO | WO 2004/091463 | 10/2004 |
| WO | WO 2004/093763 A1 | 11/2004 |
| WO | WO 2005/092401 A1 | 10/2005 |
| WO | WO 2011/022305 A2 | 2/2011 |
| WO | WO 2013/025481 A1 | 2/2013 |
| WO | WO 2013/033669 A2 | 3/2013 |
| WO | WO 2013/138394 A1 | 9/2013 |

OTHER PUBLICATIONS

Herbert et al., "Electroceramics: Materials, Properties, Applications," $2^{nd}$ Ed., John Wiley & Sons, West Sussex; 2003.

Humbeeck et al., "Characteristics of Shape Memory Alloys," *Shampe Memory Materials*, Chapter 7, Cambridge University Press, Cambridge; 1999.

International Preliminary Report on Patentability completed Apr. 23, 2007, for International Application No. PCT/EP2005/010886.

International Preliminary Report on Patentability dated Jul. 29, 2008, in Europe, Patent Application No. PCT/GB2007/000244. 6 pages.

International Search Report dated Feb. 16, 2006, for International Application No. PCT/EP2005/010886.

International Search Report dated Apr. 17, 2007, in Europe, Patent Application No. PCT/GB2007/000244. 4 pages.

International Search Report dated May 10, 2006, for International Application No. PCT/EP2006/000276, published as WO 2007/079777 A1.

Toshiiku et al., "An Introduction to Ultrasonic Motors," Chapter 1, Claredon Press, Oxford; 1993.

Written Opinion dated Jan. 24, 2007, in Europe, Patent Application No. PCT/GB2007/000244. 5 pages.

Zhang et al., "Electroactive Polymer (EAP) Actuators as Artificial Muscles: Reality, Potential, and Challenges," $2^{nd}$ Ed., Chapter 4, SPIE Press, Bellingham; 2004.

\* cited by examiner

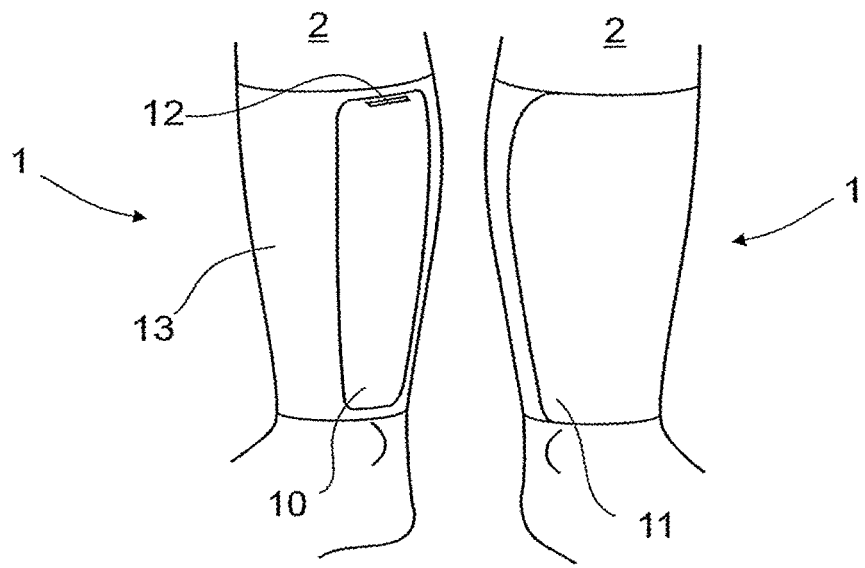
Fig 1a Fig 1b
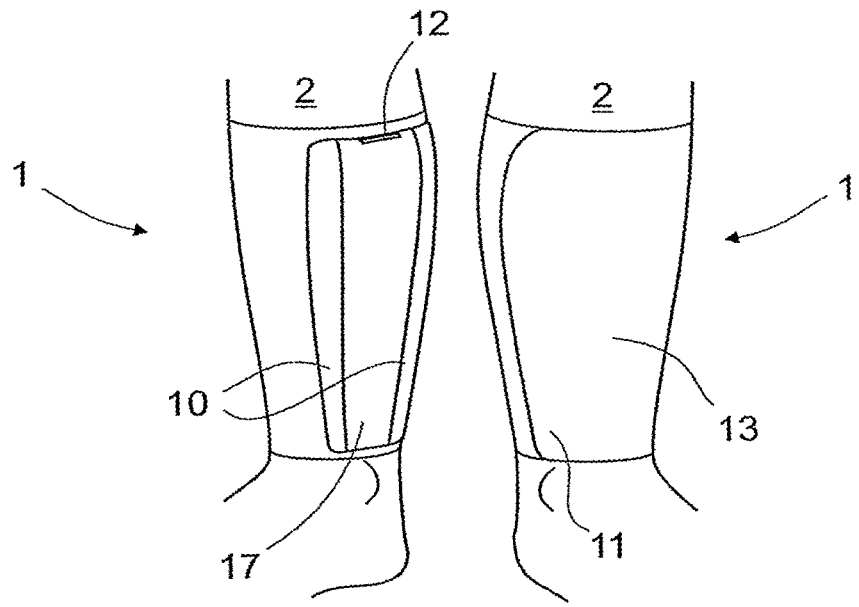
Fig 1c Fig 1d

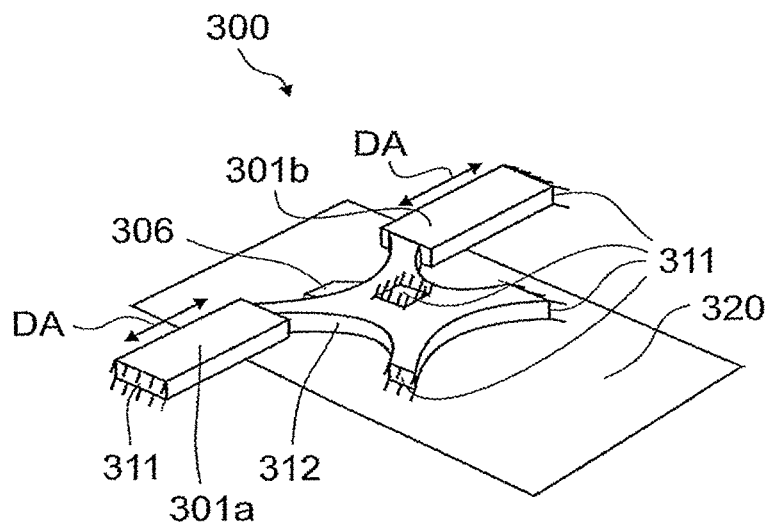
Fig 6a
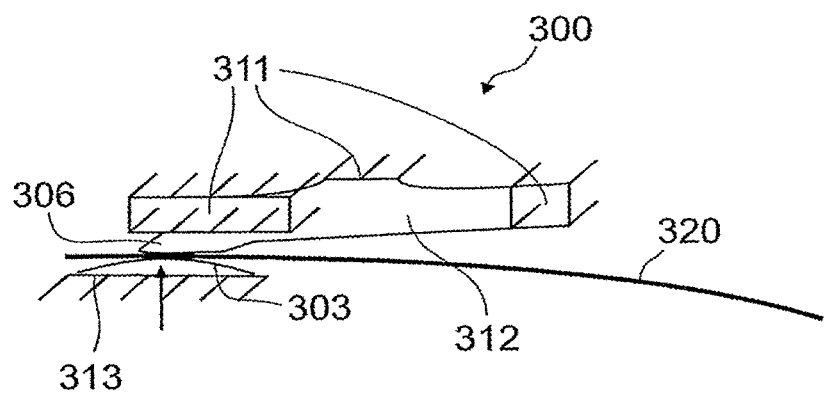
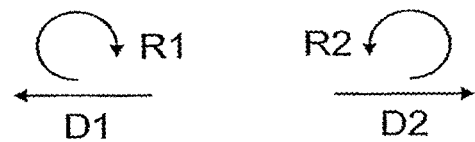
Fig 6b

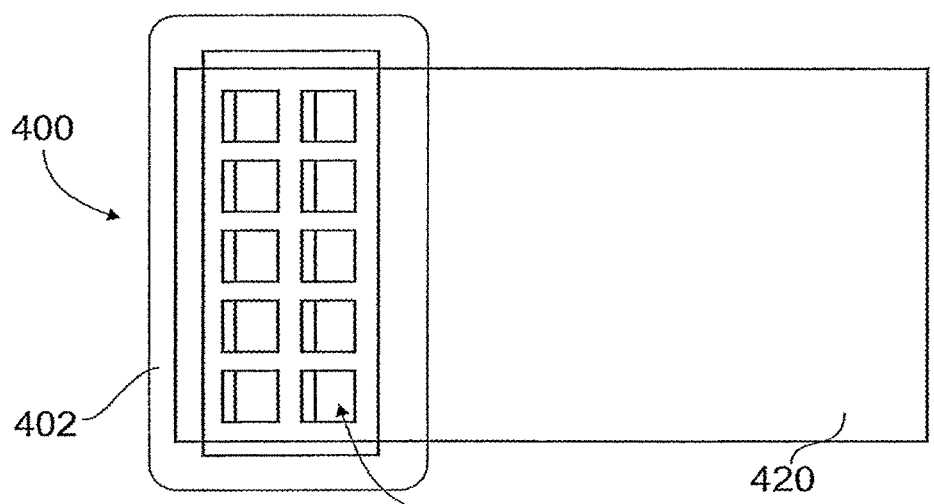
Fig 7a
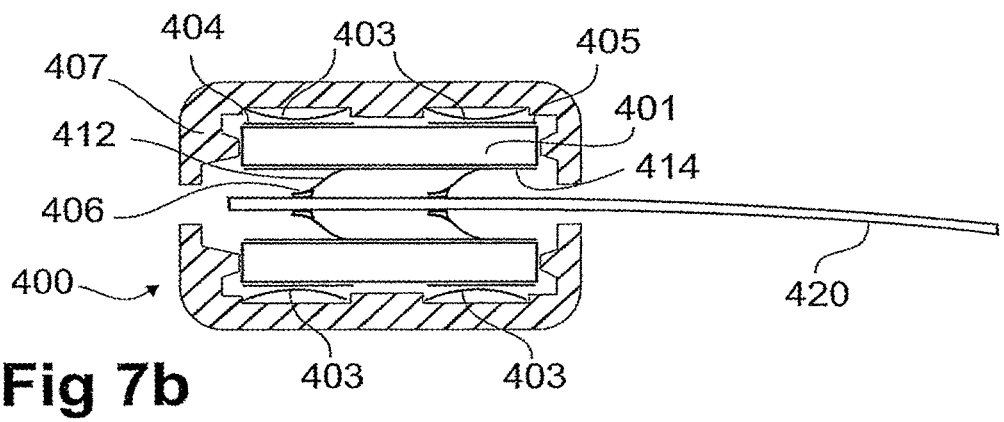
Fig 7b
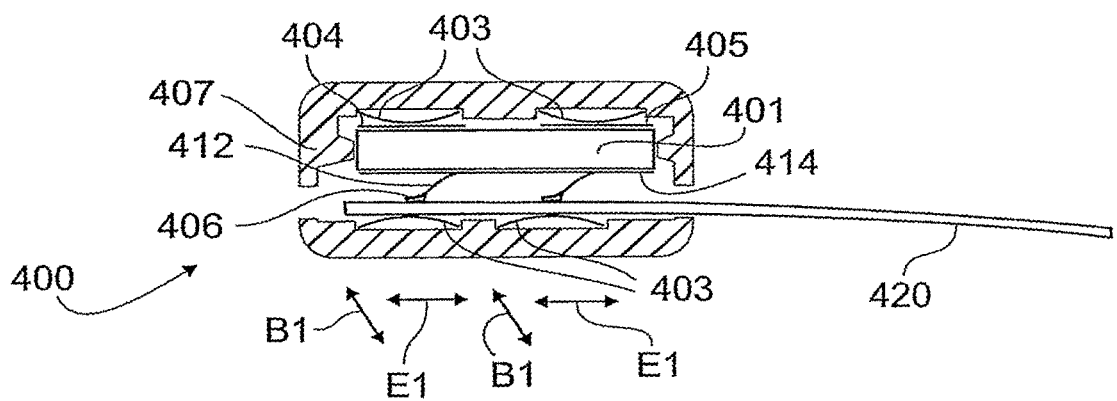
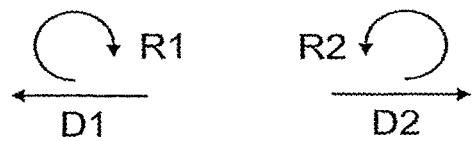
Fig 7c

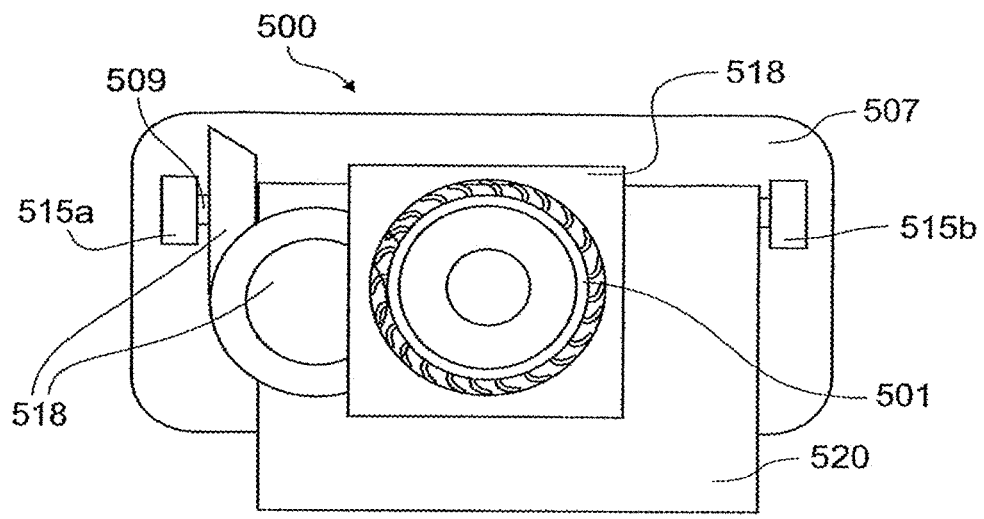
Fig 8a
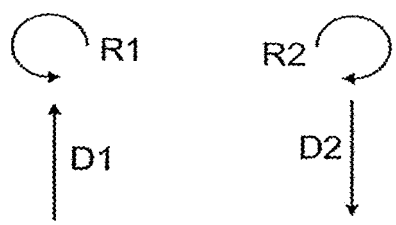
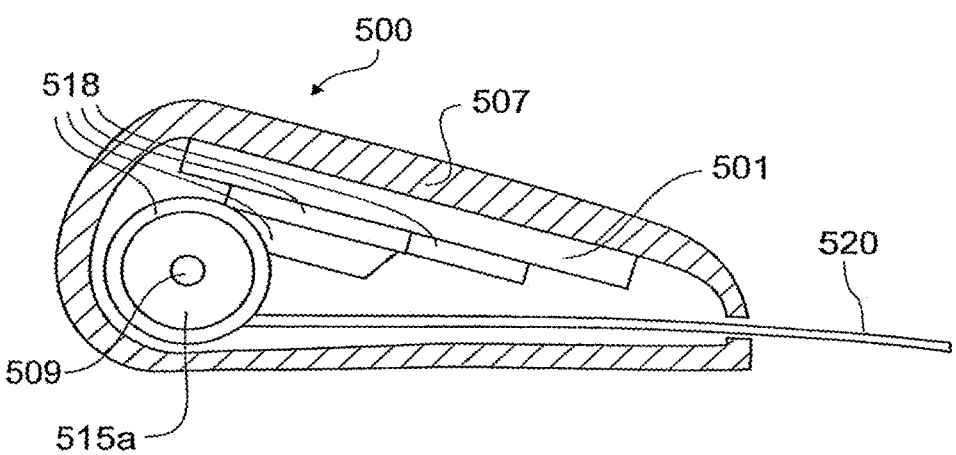
Fig 8b

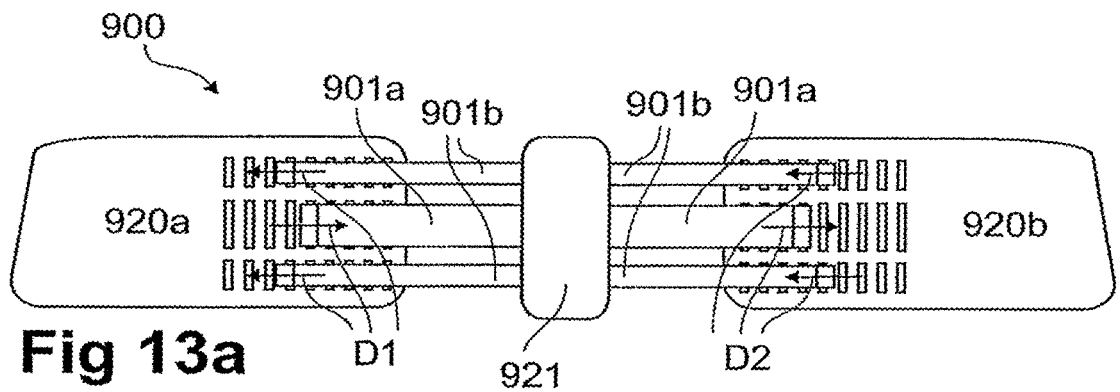
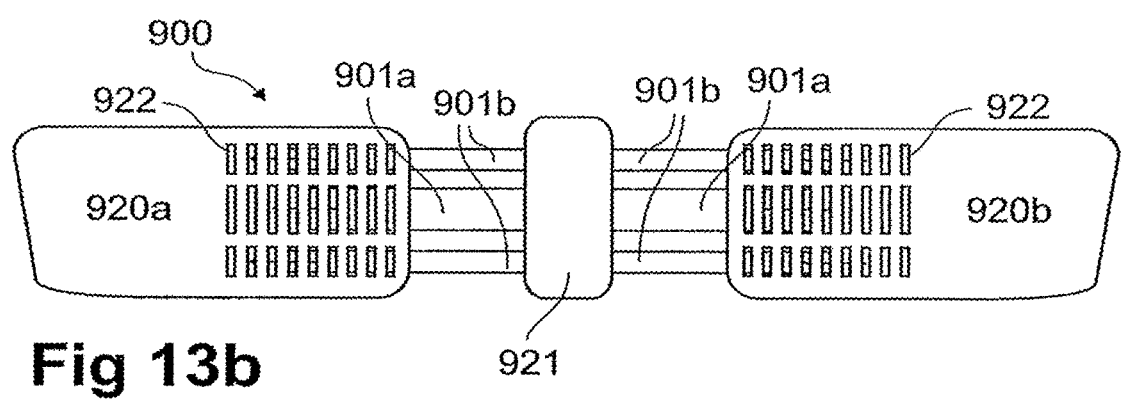
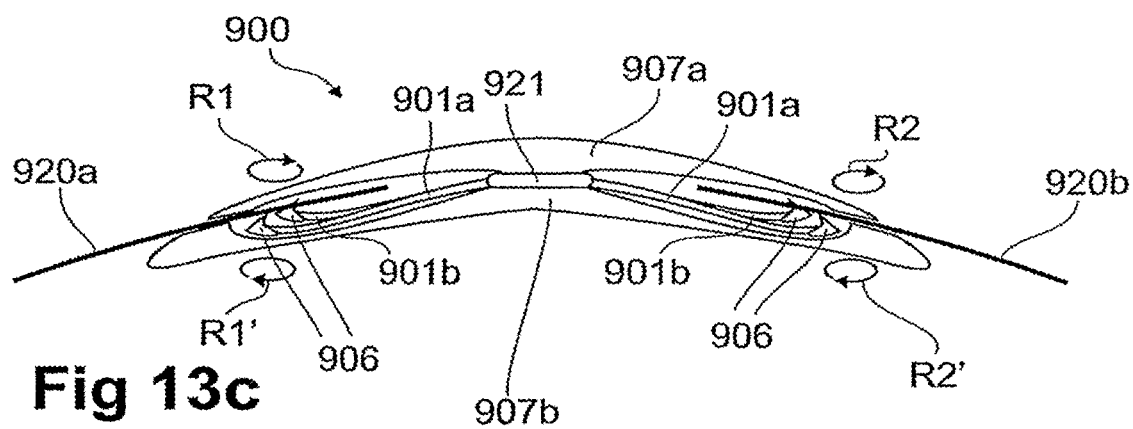

DEVICE, SYSTEM AND METHOD FOR COMPRESSION TREATMENT OF A BODY PART

The present application is a continuation application of U.S. patent application Ser. No. 14/299,201 filed on Jun. 9, 2014, which is a continuation application of U.S. patent application Ser. No. 12/160,674, filed on Feb. 10, 2009 (now U.S. Pat. No. 8,764,689), which is a U.S. National Stage of International Application PCT/EP2006/000276, filed on Jan. 13, 2006, all of which are incorporated herein by reference.

TECHNICAL FIELD

The present disclosure relates to a device for compression treatment of a body part. The disclosure also relates to a system for compression treatment, comprising such a device and to a method of compression treatment, using such a device.

The disclosure further relates to actuators that can be used in the device for compression treatment, but also in other applications where a strap is to be tightened around an object.

BACKGROUND

Compression therapies may be used for treatment and/or prophylaxis of a number of conditions, including, but not limited to, Deep Vein Thrombosis (DVT), vascular disorders, circulatory disorders, edemas, heart conditions (treated by counterpulsation), lymphedema, burns and embolisms. Other areas of use may be stress therapy, massage therapy, blood pressure monitoring, fit adjustment mechanisms for prostheses and suits for preventing pooling of blood in body parts of pilots or race car drivers subjected to G-forces.

US 2004/0073146 A1 discloses a portable device for enhancing blood flow in a limb with a view to decreasing the risk of developing a Deep Vein Thrombosis. The device comprises a strap, which is wound around the limb, and a housing comprising a motor, which is arranged pull the strap by a reciprocating motion, such that a compressive force is applied to the limb.

The motor of US 2004/0073146 A1 is of an electromagnetic type, which provides low power to weight ratio, and thereby a very bulky device. When combined with the low efficiency of the disclosed motors and power transmission elements, the result is a short battery life. Furthermore, the device would require a complex locking mechanism for holding the pressure during a period longer than that of the reciprocating motion. Also, due to the torque capabilities of conventional electromagnetic motors, it would be difficult to meet the force requirements for Deep Vein Thrombosis prophylaxis using this technology and in a compact format. Furthermore, as the reciprocating motion is produced through an intermediate mechanism and the tissue mechanics of every patient are different, there will be little to no control of the actual force output applied by the straps onto the patient.

US 2002/0173735 A1 discloses a device for external counter pulsation treatment of a heart disease or circulatory disorder. The device comprises a cuff, which is to be wrapped around a patient's extremity. The ends of the cuff are attached to each other such that electrical activation of actuators of the cuff will cause it to constrict. The actuators may be solenoid actuators, which typically provide a reciprocating motion.

The device of US 2002/0173735 A1 is only suitable for impulse applications, since the solenoid actuator cannot be made to retain a force for a period longer than that of the reciprocating motion, since a very high current would be required to provide for low frequency or static operation. This device also provides low power to weight ratio, resulting in a heavy device. Furthermore, the device is only capable of providing small motions, due to the tight fitting requirements of the cuff.

Furthermore, solenoid actuators are only capable of providing small motions, thereby placing tight fitting requirements on the cuff. Motion limitations of the actuators will also limit the actual forces that one can apply to the patient as the patient's tissue compliance will have to be overcome to reach significant force levels.

U.S. Pat. No. 6,494,852 B1 discloses a portable ambulant pneumatic compression device, comprising a sleeve having inflatable cells, which are coupled to a conduit delivering a fluid from a control device.

The use of pneumatic actuation as disclosed in U.S. Pat. No. 6,494,852 B1 also provides low power to weight ratio and thereby makes the device bulky. Furthermore, efficiency of pneumatic devices is low, as they waste much energy in their compressors, valves, accumulators, conduits, and bladder expansion, in addition to wasting energy on each deflation cycle by venting the compressed air to the surroundings. Hence, such a device requires an oversized power unit and will provide short battery lives. The use of pneumatic bladders also results in bulky, nonbreathable garments around the patient's limb.

Compression devices having straps or cuffs comprising active material, that are intended to be wound around a body part, are illustrated in U.S. Pat. Nos. 5,997,465, 6,123,681, 6,198,204 B1, EP 1 324 403 A1, US 2004/0167375 A1, WO 2004/093763 A1 and US 2005/0043657 A1. These devices generally require large amounts of active material, and are therefore at present only suitable for high-cost applications. Some of the concepts shown in these documents also require active materials having properties that cannot be achieved in large scale production or cannot be maintained over many actuation cycles with known materials.

Each of the configurations of the prior art would place undue burden on the active material properties. The materials are required to perform extreme combinations of stroke and force against patients, with widely varying geometry and tissue compliance. Therefore either excessive material or very high performance material is needed for the devices, leading to both high cost devices and increased reliability and safety issues in practical devices.

Hence, there is a need for an improved device for compression treatment of a body part.

SUMMARY OF THE INVENTION

One objective of this disclosure is to provide a device for compression treatment of a body part, which eliminates or at least alleviates some or all disadvantages of the prior art.

One particular objective is to provide a device for compression treatment of a body part, having an improved power to weight ratio.

Yet another objective is to provide a device for compression treatment of a body part, which can be produced at a reasonable cost.

Yet another objective is to provide a device suitable for ambulatory treatments with a long battery life.

Yet another objective is to provide a safe and easy to use means of applying compression treatments.

Yet another objective is to provide a device for compression treatment, which can be made very compact and which can exhibit a low height from the body part and outwards.

The above objectives are wholly or partially met by devices, systems and methods according to the appended independent claims. Embodiments are set forth in the appended dependent claims, in the following description and in the annexed drawings.

According to a first aspect, there is provided a device for compressive treatment of a body part. The device comprises a compression member, adapted to at least partly encircle the body part, and an actuation unit, arranged to tighten the compression member to provide a compressive force to the body part. The actuation unit comprises an active material actuator. By "active material" is understood a material that exhibits strong coupling between energy storage mechanisms (strong being relative to coupling observed in other common materials). In particular, with respect to this disclosure, the term "active material" is intended to cover materials that exhibit strong coupling between electrical, chemical or thermal and mechanical energy storage mechanisms (electromechanical, thermo-mechanical, electro-thermo-mechanical or electro-chemo-mechanical).

Such materials have been categorized by the research community. Generally, such active materials are categorized into the following groups: electroactive polymers, electroactive ceramics and crystals, and shape memory materials.

Electroactive polymers (EAP) comprise E-field activated materials, such as ferroelectrics, piezoelectric, electrostrictive, electrets, liquid crystal elastomers, Maxwell stress activated elastomers and composites thereof. Electroactive polymers also comprise electrochemically activated conducting polymers, ionomeric polymer metal composites (IPMC), carbon nanotubes and electroactive polymer gels. Materials of this type are described and characterized in Bar-Cohen Y. (editor): *Electroactive Polymer (EAP) Actuators as Artificial Muscles: Reality, Potential, and Challenges,* 2nd Edition, SPIE Press, Bellingham, 2004.

Electroactive ceramics and crystals comprise piezoelectric, electrostrictive and piezoceramic-polymer composites, magnetostrictive materials and single crystal materials. Materials of this type are described and characterized Moulson A. J., Herbert J. M.: *Electroceramics: Materials, Properties, Applications,* 2nd Edition, John Wiley & Sons, West Sussex, 2003.

Shape memory materials include shape memory alloys, which may be temperature activated or H-Field activated, and shape memory polymers. Materials of this type are described and characterized in Otsuka K., Wayman C. M.: *Shape Memory Materials,* Cambridge University Press, Cambridge, 1999.

It is recognized that in this rapidly evolving field that new materials are constantly being discovered or engineered. New active material actuators, possibly with exceptional performance, could be developed from such new materials and as such, the embodiments in this application could be implemented with such advanced actuators (and benefit from increased forces, power density or movement rate).

By using an active material actuator, it is possible to provide a compact compression device, which may be produced at a low cost, and which may be provided with sufficient force capability.

The actuation unit may be arranged to stepwise tighten the compression member. By stepwise tightening the compression member, it is possible to utilize actuators that are capable of very small movements, which are repeated to provide a sufficient movement.

In the device, a gripping member may be connected to the actuator to perform a cyclic motion, and the gripping member may be arranged to engage a movable member, connected to the compression member. The cyclic motion may be e.g. asymmetric, elliptical, substantially circular or substantially reciprocating.

The movable member may, during a first part of the cyclic motion be movable with the gripping member, and during a second part of the cyclic motion be movable relative to the gripping member. Hence, during the first part of the cyclic motion, there may be no or very little relative motion (slippage) between the gripping member and the movable member, and during the second part of the cyclic motion, there may be slippage between the gripping member and the movable member, or complete disengagement.

During the first part of the cyclic motion, the gripping member may be in a force-transferring engagement with the movable member, and, during the second part of the cyclic motion, the force-transferring engagement may be eliminated or substantially reduced.

The device may further comprise means for biasing the movable member and the gripping member towards each other. Such biasing means may increase the force capability of the actuation unit, and may take the form of e.g. springs or other elastic elements.

The gripping member may be provided with a wear resistant coating. Such coatings are per se known to the skilled person.

The gripping member may be provided with a grip-enhancing coating. Such coatings are per se known to the skilled person.

The actuation unit may further comprise a second actuator and a second gripping member. The first and second gripping members may be coordinated and operate simultaneously or in an alternating manner.

The gripping member and the second gripping member may be arranged on opposite faces of the movable member.

Alternatively, or as a complement, the gripping member and the second gripping member may be arranged on the same face of the movable member.

A frequency of the cyclic motion may be in the range of about 1 to 200 Hz, about 0.2 to 20 kHz or about 20 kHz to 1 MHz.

The device may further comprise rectification means for providing a one-way motion of the movable member. Such rectification may increase the force capability by reducing or eliminating slippage between the gripping member and the movable member.

According to a first principle, the actuator may comprise an active region extending parallel with a direction in which the movable member is displaceable, wherein the movable member has a substantially planar or slightly curved portion facing the actuator, and wherein the gripping member protrudes from the actuator towards the movable member.

The active region is the part of the actuator which provides the motion.

In a first embodiment, amplification means may be provided by means of a morphology of the active material.

The actuator may comprise at least two electrode sets, each electrode set being operatively connected to an active material region of the actuator and individually controllable, and wherein the active material region of the actuator is operatively connected to the gripping member.

The electrode sets may be controllable to control the movable member's direction of motion.

A first one of the electrode sets may be controllable to move the movable member in a first direction, and wherein the second electrode set may be drivable to move the movable member in a second, opposite direction.

The actuator may have at least one favorable resonant or anti-resonant frequency, and wherein at least one of the electrode sets may be drivable at said favorable resonant or anti-resonant frequency.

The rectification means may be provided by the gripping member, during a portion of the cyclic motion wherein the gripping member is movable relative to the movable member, being movable in a first direction a distance, which is greater than a distance by which a counterforce provided by a system comprising the body part and the compression member during said portion of the cyclic motion is capable of moving the movable member in a second, opposite direction.

In a second embodiment, the rectification means may be provided by the actuation unit comprising at least two gripping members, each gripping member being individually controllable to perform a respective cyclic motion.

In this embodiment, the gripping members may be arranged to be driven with a delay between their respective cyclic motions, such that, at any point in time, at least one of the gripping members is in force-transferring engagement with the movable member.

According to a second principle, the active material may be connected to the gripping member via amplifying means.

The amplifying means may comprise a wave guiding and/or wave shaping member, or an equivalent structure.

The active material and the amplifying means may be so arranged that a first driving frequency applied to the active material provides a first direction of the gripping member's cyclic motion, and a second, different, driving frequency applied to the active material provides a second, opposite direction of the gripping member's cyclic motion.

The rectification means may be provided by the gripping member, during a portion of the cyclic motion wherein the gripping member is movable relative to the movable member, being movable in a first direction a distance, which is greater than a distance by which a counterforce provided by a system comprising the body part and the compression member during said portion of the cyclic motion is capable of moving the movable member in a second, opposite direction.

In a third embodiment, the amplifying means may comprise a resonant horn, which is connected to the gripping member and to a housing or frame of the actuation unit.

The actuator may provided at an outer edge of the resonant horn. For example, the actuator may be provided at a node of the resonant horn.

The resonant horn may have a cross section, which tapers towards the gripping member.

In a fourth embodiment, the amplifying means may comprise a fin or an arm extending from the actuator to the gripping member.

At least two fins may extend from the actuator to a respective gripping member.

According to a third principle, the movable member may be provided with means for positive interlocking with the gripping member. Such positive interlocking may provide said rectification means The means for positive interlocking may comprise a ratchet structure extending in a direction parallel with the movable member's direction of motion.

The means for positive interlocking may comprise at least two parallel ratchet structures.

In a fifth embodiment, the ratchet structure may comprise a plurality of sequentially arranged teeth, each tooth having at least one locking surface adapted for interaction with the gripping member.

Two adjacent locking surfaces may be spaced apart by a distance which is smaller than the maximum-stroke of the actuator.

The actuator may comprise a first active region arranged to move the gripping member in a direction parallel with the movable member's intended direction of motion, and a second active region, arranged to move the gripping member in a direction away from the movable member.

The first active region may be arranged to move the gripping member in a direction parallel with the movable member's intended direction of motion at a first speed, and a movement in a second, substantially opposite, direction at a second, higher speed.

The second speed may be adapted to be sufficient to move the movable member in its intended direction of motion, in spite of a counter force from the compressed body part.

The gripping member and the movable member may, during said first and second movements, be biased towards each other.

In a sixth embodiment, a respective gripping member comprising a respective hook, may be arranged to interact with the respective ratchet structure.

The gripping members may be arranged to be driven with a delay between their respective cyclic motions, such that, at any point in time, at least one of the gripping members is in force-transferring engagement with its associated ratchet structure.

According to a fourth principle, the movable member may comprise a guide member extending substantially parallel with its intended direction of movement, whereby the gripping member comprises first and second longitudinally spaced-apart clamp members, which are controllable for releasable engagement with the guide member, whereby the gripping member further comprises a longitudinal movement member extending between said clamp members, whereby the longitudinal movement member is controllably expandable and contractable in a direction parallel with guide member.

The clamp members and the longitudinal movement member may be individually controllable.

The clamp members and the longitudinal movement member may be drivable in the following states:
  a) a locking state, whereby both clamp members are in a force-transmitting state relative to the guide member,
  b) a first movement state, whereby a first one of the clamp members is in a force-transmitting state relative to the guide member, wherein a second one of the clamp members is movable relative to the wall of the space, and wherein the longitudinal movement member is expanded or contracted, and
  c) a second movement phase, whereby the second one of the clamp members is in a force-transmitting state relative to the guide member, wherein the first one of the clamp members is movable relative to the guide member, and wherein the longitudinal movement member is expanded or contracted.

According to a fifth principle, the actuator may be arranged to cause the gripping member to perform a reciprocating motion, having a component in a plane substantially parallel with an intended direction of movement of the movable member, whereby said rectifying means are provided for: providing a high friction between the gripping member and the movable member during a first part of said reciprocating motion, wherein the gripping member moves in a first direction in said plane, and providing low friction between the gripping member and the movable member during a second part of said reciprocating motion, wherein the gripping member moves in a second, opposite direction.

The rectifying means may be provided between the gripping member and the movable member.

The rectifying means may be provided between the movable member and a base member, to which the actuator fixedly mounted.

The rectifying means may comprise inclined microfilaments.

The rectifying means further comprises a ratchet structure arranged for interaction with said inclined microfilaments.

The device may optionally comprise means for at least partially disengaging said rectifying means, so as to allow relative motion between the gripping member and the movable member in both of said first and second directions.

According to a sixth principle, the actuation unit may be arranged to control a radial distance between the body part and the compression member, or a connection member connected to the compression member.

The actuation unit may comprise a mounting base, extending between two circumferentially spaced apart portions of the compression member, or of the connection member, and wherein a controllably bendable actuator element is provided to control a radial distance between the mounting base and the compression member or the connection member connected to the compression member.

A ratchet mechanism may be provided on the mounting base for interaction with an edge of the actuator element.

Opposing edges of the actuator element may engage respective ratchet structures, and a central portion of the actuator element may engage the compression member or connection member.

In one embodiment, the movable member may be integrated with the compression member.

In one embodiment, the movable member may be formed in one piece with the compression member.

In one embodiment, the movable member may be fixedly attached to the compression member.

In another embodiment, the movable member may be connected to the compression member by a connection member.

In another embodiment, the movable member may be releasably attachable to the compression member.

According to a seventh principle, the movable member may comprise a rotatable part, which is rotatably arranged about a substantially central axis, and wherein the gripping member is arranged to act on a surface of said rotatable part.

The gripping member may be arranged to engage a surface of the rotatable part, at a distance from the central axis, wherein a spindle is rotatable about said central axis and connected to the rotatable part, and wherein the compression member or a connection member, connected to the compression member, is windable onto the spindle.

A single compression member or connection member may be windable onto the spindle.

Two or more compression members or connection members may be windable onto the spindle, and extend in essentially different directions from the central axis.

Effective diameters of the rotatable part and the spindle member may be different.

At least two rotatable parts may be connected to the spindle, and a respective actuator may be arranged to interact with said rotatable parts.

The rotatable parts may be arranged substantially at a respective end portion of the spindle.

Amplification means is provided by means of a morphology of the active material.

The actuator may comprise at least two electrode sets, each electrode set being operatively connected to an active material region of the actuator and individually controllable, and the active material region of the actuator may be operatively connected to the gripping member.

A first one of the electrode sets is controllable to move the movable member in a first direction, and the second electrode set may be drivable to move the movable member in a second, opposite direction.

The actuator may have at least one favorable resonant or anti-resonant frequency, and at least one of the electrode sets may be drivable at said favorable resonant or anti-resonant frequency.

The actuation unit may comprise two actuators, which are individually drivable.

The actuators may be drivable at different phases.

At least one of the actuators may be arranged at an acute angle relative to the movable member.

At least one of the actuators may have at least one favorable resonant or anti-resonant frequency, and at least one of that actuator's electrode sets may be drivable at said favorable resonant or anti-resonant frequency.

According to an eighth principle, the actuator may comprise a motor, selected from a group consisting of a horn excitation type motor, a standing wave rotary motor, a displaced traveling wave motor and an ultrasonic motor, the motor being operatively connected to a spindle, wherein the compression member, or a connection member, connected to the compression member, is windable onto the spindle. Such a motor may be a rotary motor.

The motor may be connected to the spindle via a power transmission mechanism.

A single compression member or connection member may be windable onto the spindle.

Two or more compression members or connection members may be windable onto the spindle, and extend in essentially different directions from the spindle.

A rotatable output part of the motor may be coaxial with the spindle.

The compression member may mainly be formed from one or more passive materials.

Such passive materials may, however, be e.g. elastic, compressible, rigid or flexible.

At least one actuation unit may be arranged in a direction parallel with the body part, and the compression member may extend in a substantially perpendicular direction from said at least one actuation unit.

The actuation unit may be arranged to tighten two compression members extending in different directions, or two ends of a single compression member at least partly encircling the body part.

At least two actuation units may be arranged in parallel, each actuation unit being arranged to tighten at least one compression member.

The actuation units may be arranged to tighten the compression members by pulling them in opposite directions.

According to a second aspect, there is provided a device for compressive treatment of a body part, the device comprising an actuation unit, adapted to at least partly encircle the body part, the actuation unit being arranged to provide a stepwise compressive force to the body part, the actuation unit comprising an active material actuator, i.e. a material, which, upon electrical or electrochemical stimulation, changes its geometric properties.

The active material actuator may be expandable and contractable in a circumferential direction.

The active material may have an expansion speed, which is higher than a contraction speed.

The actuation unit may comprise first and second portions, which are displaceable relative to each other in a substantially circumferential direction, the first portion being provided with a ratchet structure and the second portion being provided with a gripping member.

The actuation unit may comprise two gripping members, each gripping member's interaction with the ratchet structure, or a respective ratchet structure, being individually controllable.

The gripping members may be arranged to be driven with a delay between their respective cyclic motions, such that, at any point in time, at least one of the gripping members is in force-transferring engagement with its associated ratchet structure.

The gripping member may be arranged at an outermost edge of the second portion.

The ratchet structure and the gripping member may be biased towards each other.

The gripping member may comprise a second actuator controlling a bendable element, arranged to engage said ratchet structure to maintain the compressive force to the body part.

The actuator and the bendable element may form a bi-layered structure.

The bendable element may be arranged to substantially enclose an outer edge of the second portion.

The bendable element may be formed in one piece with the active material actuator.

A portion of the bendable element that is designed to contact the ratchet structure may be provided with a grip and/or wear enhancing coating.

The device may be sized and adapted to form a sleeve around the body part.

The device may be formed as a sheet having opposing edge portions provided with connection means for connecting said edge portions to each other to form said sleeve.

The actuation unit and the compression member, if any, may form an active layer, the device may comprise at least one of: a sensor layer, arranged between the active layer and the body part; an inner layer, arranged between the sensor layer, or the active layer, and the body part; and an outer layer, arranged outside the active layer.

The inner layer and the sensor layer may be integrated to form a disposable layer.

Such a disposable layer may comprise means for mechanically and/or electrically connecting with the active layer.

Such a disposable layer may comprise means for transferring a signal from the disposable layer to the active layer or to an control unit, which is external to the device.

According to a third aspect, there is provided a system comprising a device as described above, and a control unit, connected to the device and arranged to provide a control signal to the device.

In the system, the device may comprise a sensor layer including at least one sensor element, wherein the control unit is arranged to receive a feedback signal from the sensor.

The control unit may be at least partially integrated with the device.

According to a fourth aspect, there is provided use of a device for compressive treatment of a body part as described above, for treating and/or preventing a condition selected from a group consisting of Deep Vein Thrombosis (DVT), a vascular disorder, a circulatory disorder, an edema, a heart condition, lymphedema and an embolism.

According to a fifth aspect, there is provided use of a device for compressive treatment of a body part as described above, for preventing or counteracting pooling of blood in a body part of a person subjected to a G-force.

According to a sixth aspect, there is provided use of a device for compressive treatment of a body part as described above, for stress therapy, massage-therapy, blood pressure monitoring, or as a fit adjustment mechanism for a prosthesis.

According to a seventh aspect, there is provided non-therapeutic use of a device for compressive treatment of a body part as described above.

According to an eighth aspect, there is provided use of a device for compressive treatment of a body part as described above, for non-medical purposes. Examples of such non-medical purposes include cosmetic treatments such as cellulite reduction and breast stiffening. Other examples of non-medical treatment may include massage treatment for relaxation purposes.

According to a ninth aspect, there is provided a method for operating a device for compressive treatment of a body part, the method comprising tightening a member encircling the body part to provide a compressive force to the body part, and controlling an actuation unit of the device, connected to the member and comprising an active material actuator, to stepwise provide said compressive force.

BRIEF DESCRIPTION OF THE DRAWINGS

FIGS. 1a-1d schematically illustrate a body part, provided with a compression device.

FIGS. 6a and 6b schematically illustrate part of an actuation unit according to a third embodiment.

FIGS. 7a-7c schematically illustrate an actuation unit according to a fourth embodiment.

FIGS. 8a-8b schematically illustrate an actuation unit according to a fifth embodiment.

FIGS. 13a-13c schematically illustrate an actuation unit according to a ninth embodiment.

DESCRIPTION OF EMBODIMENTS

Figure 2:
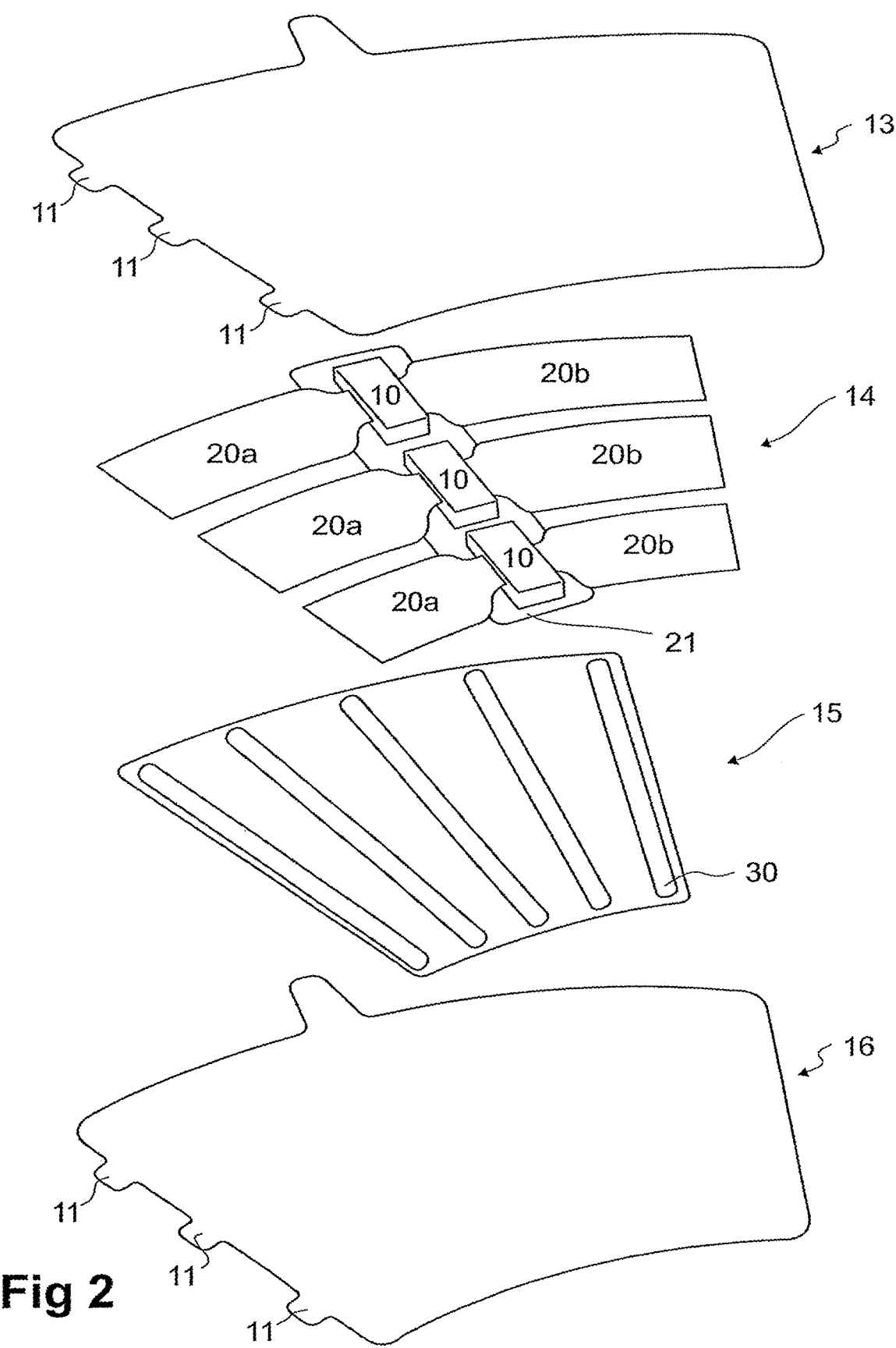
FIG. 2 is a schematic perspective exploded view of some constituents of a compression device according to an embodiment.

FIGS. 1a-1d, schematically illustrate compression devices 1 arranged around a respective body part 2. The body part illustrated is exemplifying only. It is understood that a compression device could be formed to fit any desired body part, such as a foot, a lower leg, an upper leg, a lower arm, an upper arm, a torso, abdomen etc. Each compression device 1 comprises an actuation unit 10, which may have a connector 12 for connection to e.g. an external power supply (not shown), controller (not shown) or monitoring device (not shown). Also indicated is an outer fabric 13 of the compression device 2. Furthermore, the compression device 1 may have the form of a sheet, which is to be wrapped around the body part, whereby edge portions thereof are connected to each other by an attachment arrangement 11, which may have the form of a hook-and-loop device (such as Velcro®), a zipper, buttons, strings, adhesive tape etc. As another option, the compression device could form a pull-on sleeve, i.e. a sleeve having no attachment arrangement.

In the embodiments illustrated in FIGS. 1a-1b, a single actuation unit 10 is provided, whereas, in the embodiments illustrated in FIGS. 1c-1d, two actuation units 10 are provided in parallel, with an electronics section 17, which may be arranged between the actuation units 10.

FIG. 2 is a schematic perspective exploded view of some constituents of a compression device according to an embodiment. In the embodiment illustrated in FIG. 2, the compression device comprises an outer layer 13 and an inner layer 16. For clarity, electronics, battery, cables, recharging unit etc. are not illustrated in FIG. 2.

Between the outer and inner layers 13, 16, there may be an actuator layer 14 arranged, comprising one or more actuation units 10 and, as the case may be, one or more compression members 20.

The actuation unit and compression members may be designed according to any of the embodiments described below. Combinations of such embodiments may also be provided.

In the embodiment illustrated in FIG. 2, three actuation units 10 are arranged on an optional flexible base 21, which extends in parallel with the body part 2 (FIG. 1). Compression members 20a, 20b extend from the actuators 10, so as to at least partially encircle the body part 2 (FIG. 1) when the compression member is in use.

Furthermore, an optional sensor layer 15 may be provided between the actuator layer 14 and the body part 2. The sensor layer may comprise one or more sensors or sensor arrays 30, which may be used to measure e.g. pressure (e.g. surface pressure or blood pressure), temperature, flow (e.g. blood flow), as needed in the treatment.

The sensor or sensors of the sensor layer may be connected to a control unit for providing feedback during use of the compression device.

The outer layer 13 may be selected so as to provide an attractive exterior to the compression device 2 and to protect the compression device against the external environment, e.g. fluids, dust, dander etc.

The outer layer may also be provided with a user interface, e.g. comprising one or more input devices, such as buttons etc, and/or one or more output devices, such as a display, indicating lamps etc.

The inner layer 16 may be selected so as to provide a smooth transition between the actuator layer and the body part 2. The inner layer 16 may also be selected so as to protect the compression device against fluids, dust, dander, etc. The inner layer may also be selected so as to absorb exudates. It is possible to provide the inner layer as e.g. a disposable stocking or absorbent material.

It is recognized that the inner layer may comprise several layers, each performing a different function, and some of which being disposable and/or replaceable.

Also, one or more layers may be integrated with each other. For example, an inner layer could be integrated with the sensor layer, an outer layer could be integrated with the actuator layer and the sensors could be integrated on e.g. the inside of the compression members, i.e. integrated with the actuator layer. As another alternative, the actuator layer and the inner layer, and optionally also the sensor layer, may be integrated. As yet another alternative, all layers may be integrated, optionally with the actuation unit forming a removable and reusable part.

The actuation unit 10 comprises an active material actuator, as defined above. Examples of active materials include materials such as piezoceramics, electrostrictive ceramics, magnetostrictors, H-field activated memory alloys and ferroelectric polymers (e.g. piezoelectric, electrostrictive, Maxwell-stress and composites).

Further examples of active materials include conducting polymers, carbon nanotubes, IPMCs and temperature activated memory alloys.

Yet further examples of active materials include gels, memory polymers (temperature or pH activated).

The actuation unit may be arranged to stepwise tighten the compression member, such that a desired compression stroke is produced by the actuator performing at least two, preferably a large number of movement cycles or steps.

For example, piezoceramics, electrostrictive ceramics and meanetostrictors may use tens to hundreds of thousands of cycles or steps for producing a desired compression stroke.

Memory alloys, conducting polymers, IPMCs and some ferroelectric polymers may use hundreds to thousands of cycles or steps for producing a desired compression stroke.

Some ferroelectric polymers and some conducting polymers may use tens to hundreds of cycles or steps for producing a desired compression stroke.

Generally, a large number of steps may be desirable for simplifying any existing feedback mechanism, since the pressure difference between two cycles or steps may be negligible.

Furthermore, in view of the cyclic behavior of the actuator, in order to provide a motion for tightening the compression member 20 around the body part, rectification means may be needed, or otherwise the compression member would merely move back and forth with a frequency corresponding to that of the actuator operation frequency, and with a very low, practically ineffective, amplitude for compressing the underlying body part.

In some embodiments, the rectification means may be provided by means of the actuator performing an asymmetric or elliptical motion. For example, an asymmetric motion may be provided by the actuator morphology, and may be provided by benders, stacks, cymbals, multi-DOF actuators. Optionally, two or more actuators may operate in parallel with a phase lag to produce the movement, in which case the actuators may also be symmetric.

Rectification means may also be provided by driving the active material in a resonant or anti-resonant vibration mode, e.g. using multiple electrodes, asymmetrically shaped actuators, coupled modes, traveling waves or even multiple actuators.

An interfacing mechanism may be provided between the actuator and a gripping member, performing the asymmetric or elliptical motion. Use may be made of the interfacing mechanism's resonant or anti-resonant modes, e.g. by giving it a suitable shape. The interfacing mechanism may also be used for providing amplification of the movement.

It is also possible to use multiple actuators operating in parallel with a phase lag.

Yet another alternative is to provide micro or meso scale ratchets on the gripping member or on the movable member. It is also possible to provide a principle actuator for the advancing or retreating movement and a secondary actuator for controlling the interaction between the gripping member and the movable member.

It is further recognized that using a "hopping" actuator may require the hop frequency to be higher than the dynamic characteristics of the body and compression member, so that the compression member will not move (slip) inadvertently with respect to the actuation unit during the part of the actuator cycle when there is little or no force being transferred.

Also, if silent operation is desired, the hop frequency should be more than 20 kHz.

Lower frequency hopping may be combined with an inertial locking arrangement to prevent slippage.

"Double clamping" can be provided by coordinated operation of two or more actuators, wherein at least one actuator has hold of the movable member at any given time.

The embodiments disclosed herein all provide self locking on power down, either by frictional engagement or by positive interlocking, i.e. they move when power is applied and retain the movable member when no power is applied. Hence, the actuators only consume power during periods of movement.

The compression member may be a generally thin, optionally breathable harness or strap that is flexible and/or bendable enough to adapt to the shape of the body part. Optionally, the compression member may be resilient.

The compression member 20 may, in particular where there is only one actuation unit on one side of the body part, comprise two layers, one that moves due to the action of the actuation unit, and one that is substantially stationary relative to the body part. Preferably, the friction between the layers should be low, so as to not transfer shear forces to the body part. Alternatively, the compression member may exhibit low friction relative to the inner layer 16.

Optionally, the compression member may be shaped so as to match a contour of the body part.

The attachment arrangement 11 may be provided on, or connected to, the compression member 20.

The compression member 20 may be provided in different sizes or lengths, and may be exchangeable, to fit differently sized body parts.

Also, the stiffness of the compression member 20 may be selected to fit the intended application: more stiff for DVT prophylaxis and other high speed or impulse type compression treatments, and less stiff for more pseudo-static compression treatments, such as VLU or lymphedema.

The compression member 20, together with the inner and/or outer layers 13, 16 and optionally the sensor layer 15 may be made from low-cost materials, and may be incorporated in a disposable package for reasons of sterilization or for compromises in lifetime/performance.

The description will now be directed to different embodiments of the actuation unit 10.

Most of the following embodiments are intended for E-field activated materials (i.e. ferroelectrics), but may be provided using other types of active materials. For example, an electrochemically activated polymer version would require an electrolyte and a counter electrode to ensure reliable operation over several cycles. A temperature activated memory material would require a heating source (resistive or fluid/air delivery system) and a means of cooling, such as a heat sink, fluid/delivery or Peltier device.

The devices may have slight differences due to the expansion/contraction characteristics of the materials. For example, polymers and ceramics, when excited, often expand along a principal axis, while contracting along another axis, whereas memory alloys can be made to contract. The driving signals could be different in terms of voltage, current, operating frequency and waveform. Some materials, e.g. memory alloys, may require a bias spring to return them to their original configuration. Such a spring could be implemented directly into the actuator or double as a bias spring, as indicated in the examples.

In some of the disclosed embodiments, the actuator may pull directly on the compression member. However, this is not necessary, and sometimes not even desirable. Instead a connection member may be provided, which may be attached or attachable to the compression member, while another part of it interacts with the actuator. This may be desirable to prevent exudates from entering into region of actuator contact. Also, it may be desirable to use the connecting member to transform energy between the actuator and the compression member to better match body and actuator dynamics, to improve lifetime or to enable reuse of the actuator and its connection member, while the compression member may be disposable.

In all embodiments, a mechanical "fuse" may be provided to protect the user and/or the actuator against excessive forces. Examples of such fuses may be a hook-and-loop type fastener a fabric with a designed-in breaking strength, commonly used fasteners such as buttons or quick release snaps, or a super elastic/plastic fabric/material with a plateau in its stress strain behavior. Such fabrics and materials are known to the skilled person in field of medical compression.

Alternatively, a mechanical fuse may be provided by designing the gripping member and the movable member so as to slip when the force exerted by the compression member on the movable member exceeds the friction force between the gripping member and the movable member.

Figure 3:
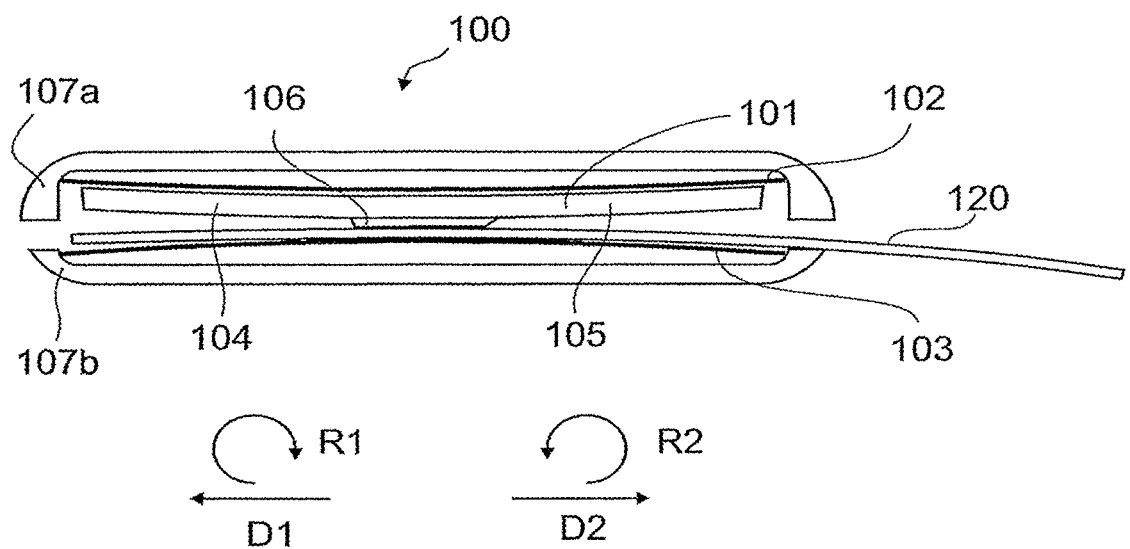
FIG. 3 is a schematic sectional view of an actuation unit according to a first embodiment.

FIG. 3 is a schematic sectional view of an actuation unit 100 according to a first embodiment, which may be arranged as indicated in FIGS. 1a-1d, 2 and 4. As a non-limiting example, this embodiment may be provided using a resonant active material multiple electroded bender. In such a device, rectification may be achieved by a friction interface. The actuation unit 100 may extend in a direction perpendicular to the section, along the entire or part of the compression device 1.

The actuation unit 100 comprises a housing 107a, 107b, wherein a first part 107a of the housing holds a flexible substrate 102, on which an actuator 101 is arranged. The actuator has a gripping member 106 protruding from the actuator and towards the second part 107b of the housing. The second part of the housing holds a bias spring 103.

A movable member 120, which may be integrated with or connected to the compression member, is clamped between the bias spring 103 and the gripping member 106. The flexible substrate 102 may be arranged to provide additional biasing of the gripping member 106 towards the movable member 120.

The actuator 101 may be provided as a resonant active material, having built-in amplification, rather than a separate amplification mechanism. By using two electrode sets 104, 105, the actuator 101 and thereby also the gripping member 106, can in a per se known manner, be given a two-dimensional movement, as indicated by reference numerals R1 and R2. The phase between the electrodes can be used to control direction (R1 or R2) and speed of the gripping member's motion. Also, the power density will be higher if both electrode sets 104, 105 are driven than if they are excited individually.

Details on how to provide the actuator may be found in U.S. Pat. No. 6,765,335 B2, US 2002/0074901 A1 and U.S. Pat. No. 6,870,304, the entire contents of which are incorporated herein by reference.

The force capability of this embodiment is largely determined by the bias spring, the attainable amplitude of the out of plane bender motion and the equivalent elasticity of the movable member 120 and the actuator 101. Also, the provision of a high strength flexible substrate 102 increases the force capability by providing support for the active material, better acoustic quality and higher fatigue strength, allowing a larger biasing force between the gripping member and the movable member, without damaging the active material. This also allows for shaping the vibration waves for resonant operation.

Thus, the direction of movement (D1 or D2) of the movable member 120 is controlled by the movement (R1 or R2) of the gripping member 106.

Figure 4:
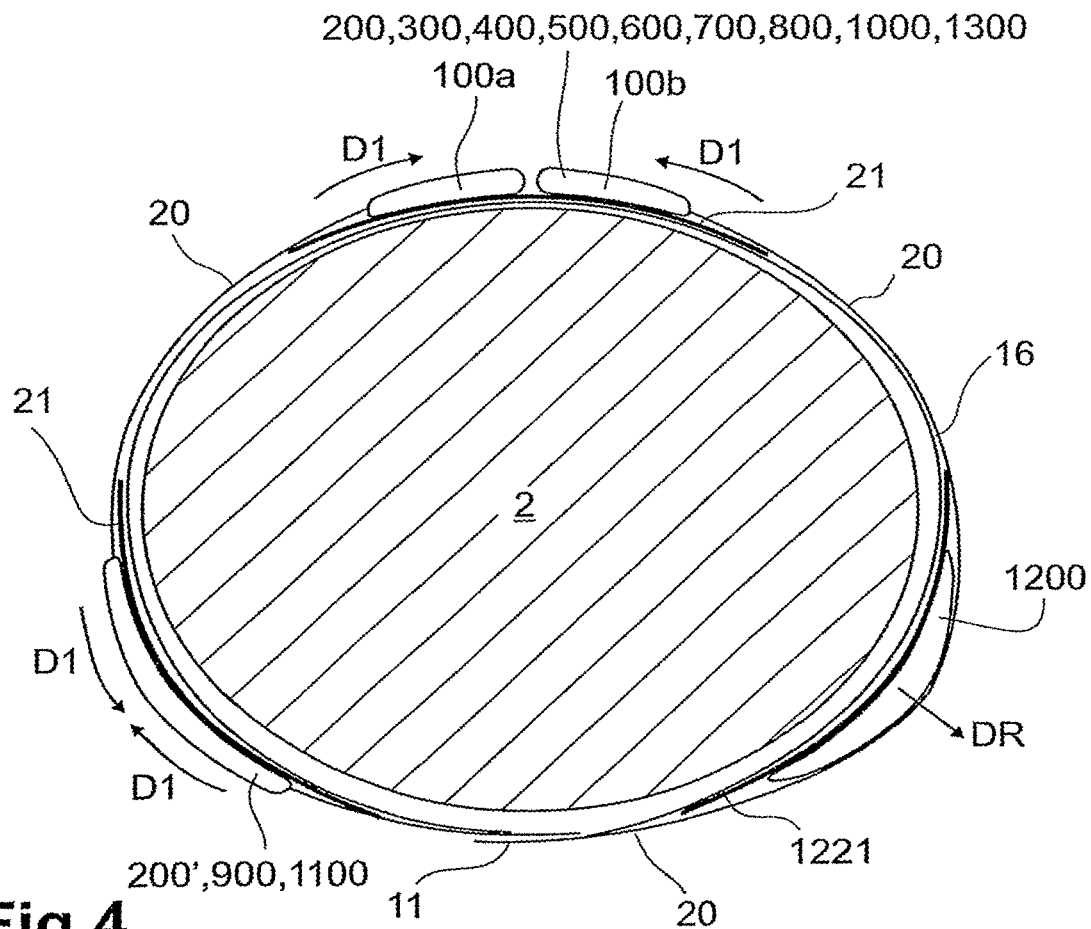
FIG. 4 is a schematic cross sectional view of a body part provided with a compression device.

FIG. 4 is a schematic cross sectional view of a body part 2 provided with a compression device. For illustration purposes, this compression device comprises four actuation units 100a, 100b, 200, 300, 400, 500, 600, 700, 800, 1000, 1300, 200', 900, 1100 and 1200, which may be selected arbitrarily from those described in the present disclosure.

A first actuation unit arrangement is provided in the upper part of FIG. 4, this arrangement comprising two single-direction actuator units, 100a, 100b, 200, 300, 400, 500, 600, 700, 800, 1000, 1300, which are arranged on a flexible base 21 and connected to a respective movable member, which may be integrated with or connected to the compression member 20. The actuator units 100a, 100b each pull on a respective compression member 20 in the direction D1 to tighten the compression member.

A second actuation unit arrangement is provided in the lower left part of FIG. 4, this arrangement comprising a two-direction actuation unit 200', 900, 1100, i.e. an actuation unit arranged to simultaneously pull on two compression members 20. This actuation unit may also be mounted on a flexible base 21.

A third actuation unit arrangement is provided in the lower right part of FIG. 4, this arrangement comprising a radially expanding actuation unit 1200, which pulls by expanding in a radial direction DR may pull one or two compression members 20.

This actuation unit may also be mounted on a flexible base 1221.

Furthermore, in FIG. 4, there is indicated an attachment arrangement 11, which may be used to connect two edges of the compression device so as to form a sleeve, and also to adjust the size of the compression device.

It is recognized that one or more of the actuation unit arrangements may be provided, as required, in the compression device.

Figure 5A:
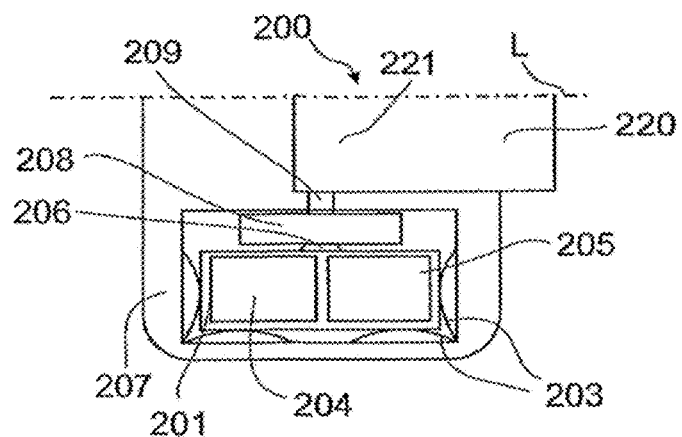
FIGS. 5a-5c schematically illustrate actuation unit according to a second embodiment.
Figure 5B:
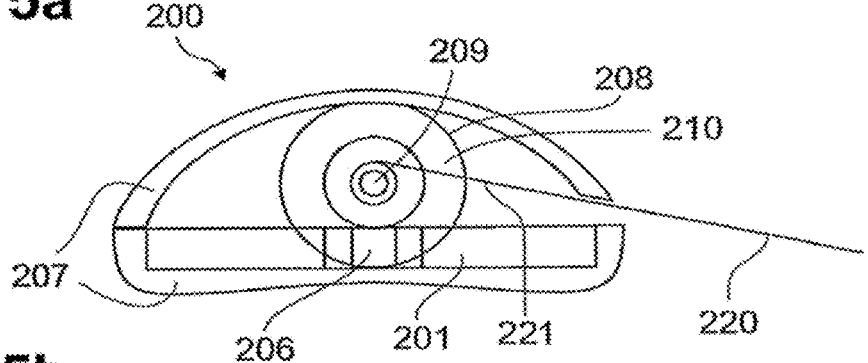
Figure 5C:
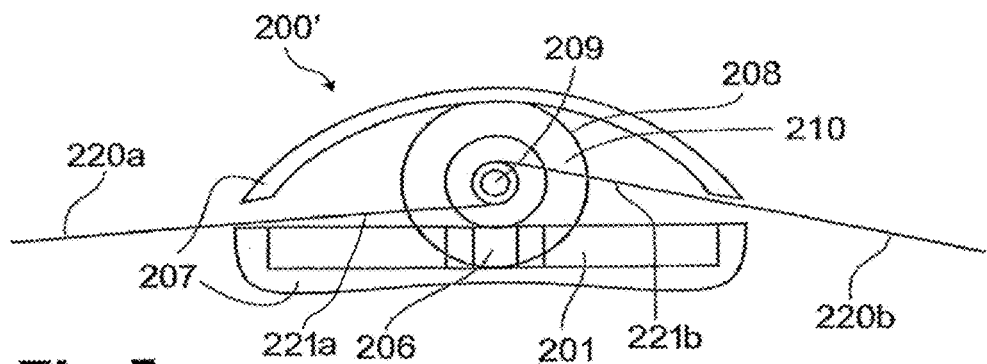

FIGS. 5a-5c schematically illustrate an actuation unit 200 according to a second embodiment, in which a power transmission mechanism 208 is provided between a gripping member 206 and a spindle 209, upon which a connection member 221 connected to the compression member 220, is wound. The actuator of FIGS. 5a-5c may use a resonant active material, such as piezoceramics, e.g. in the form of a multiple electroded stack or bulk material driven at a suitable resonant or anti-resonant frequency. FIG. 5a illustrates one half of the actuation unit 200, which may be symmetric about the line of symmetry L. The actuator 201 with the electrode sets 204, 205 and bias springs 203 may be provided in a housing 207, similar to the embodiment of FIG. 3.

However, instead of the gripping member 206 acting directly upon the compression member 220 or connection member 221, the gripping member 206 acts upon a contact surface 210 of a wheel 208 or disc shaped structure. Hence, the wheel 208 forms a movable member. The contact surface 210 may be provided at an outer diameter of the wheel, whereby the spindle 209, having a smaller diameter, may be fixedly connected to, and rotatable with, the wheel 208, about a common axis. Hence, the ratio between the contact surface 210 and the spindle will constitute a gear ratio of the power transmission mechanism.

FIG. 5b illustrates a single direction actuation unit 200, whereas FIG. 5c illustrates a two direction actuation unit 200' pulling on two compression members 220a, 220b via two connection members 221a, 221b, respectively.

The wheel 208, or at least the contact surface 210 may be made from a wear resistant material, such as a ceramic or a metal.

The actuation unit 200, 200' may be provided with a single actuator, or with dual actuators, operating on wheels placed at different ends of the spindle 209. The phase between the electrode sets can be used to determine direction of motion and speed.

Other transmission mechanisms than a spindle may be used.

The actuator of FIGS. 5a-5c may, as an example, also be designed similar to that of FIG. 3, reference being made to U.S. Pat. No. 6,765,335 B2, US 2002/0074901 A1 or U.S. Pat. No. 6,870,304, the entire contents of which are hereby incorporated herein by reference.

FIGS. 6a and 6b schematically illustrate part of an actuation unit 300 according to a third embodiment, the actuator of which can be provided by a resonant motion amplification mechanism utilizing multiple vibration modes or coupled vibration modes of a resonant horn or actuator.

In FIGS. 6a and 6b, the housing has been left out for clarity. A pair of actuators 301a, 301b, have been arranged with a respective fastening point 311 to a housing or frame of the actuation unit 300, and connected to an amplifying structure 312, which may be e.g. a micro-molded horn of metal or low acoustic loss polymer. The horn may have one or more further fastening points to the housing or frame of the actuation unit 300.

Furthermore, the amplifying structure 312 may be provided with a gripping member 306, which is to interact with a movable member 320, which may be the compression member or a connection member connected thereto. A bias spring 303 may be arranged between a fastening point 313 and the movable member 320, such as to provide a friction force between the gripping member 306 and the movable member 320.

The gripping member 306 and/or the movable member 320 may be provided with a wear resistant coating, such as chrome, ceramic or an engineered polymer coating. The gripping member 306 and/or the movable member 320 may also be provided with a friction enhancing coating or surface structure. The actuators 301a, 301b may be driven at predetermined frequencies for causing the amplifying structure 312 to provide an advancing or retreating movement (R1, R2) of the gripping member 306 and a corresponding advancing (tightening) R1 or retreating (releasing) D2 movement of the movable member 320.

To enable a high force to be achieved, the actuator should be positioned at side nodes of the resonant horn 312 as illustrated in FIG. 6a. Also, asymmetry in the gripping member movement enhances force capability by providing a gripping member force vector towards the movable member, which is inclined relative to the movable member and having components both parallel with and perpendicular to the intended direction of movement D1.

Additional force capability may be provided by providing dual actuators, one on each face of the movable member 320.

It is also possible to arrange the amplifying structure 312 so that the gripping member 306 will act upon a transmission mechanism, as was described with respect to FIGS. 5a-5c, FIG. 9 and FIG. 17. Such a transmission mechanism may further increase force capability.

The appropriate excitation frequencies for this configuration depends highly on the form of the resonant horn structure. The lateral and transverse movement of the gripping member can be determined as functions of frequency. Those functions may, in turn, be determined by the shape, fastening points, actuator inputs and mechanical properties of the resonant horn. In particular, the horn shape can have a major effect on the achievable level of amplification. As the horn shape is necked down to the gripping member, the vibration amplitude within the material will increase in correspondence with the necking. Thereby, the maximum vibration amplitude can be achieved at the gripping member and the resulting force output can be maximized. Generally computer simulation is required to optimize the parameters for a particular design.

The horn illustrated in FIGS. 6a-6b is not a production-ready embodiment, and may therefore need optimization in terms of the camber of the incline towards the gripping member, angles of each leg of the horn, actuator and fastening point positioning, material selection at the fastening point (attachment method), required gripping member size and general equations of the mold outline to maximize wave channeling, and due consideration of manufacturing tolerances.

Preferred actuators for the embodiment of FIGS. 6a6b include E-field activated polymer materials, ceramic/crystal materials, magnetostrictive materials or H-field activated memory material.

The illustrated direction DA of movement of the actuator are merely one option, and may also need optimization as described above.

FIGS. 7a-7c schematically illustrate an actuation unit 400 according to a fourth embodiment, which can be provided as an actuator similar to the one described with respect to FIGS. 6a and 6b.

In this embodiment, the actuation device 400 comprises a housing 407 and one or more actuators 401, which extend in a plane that is substantially parallel with a plane in which the movable member 406 is to move. From a surface of the actuator facing the movable member 420, a plurality of gripping members 406 protrude, whereby a respective amplification structure 412 is provided between each gripping member 406 and the actuator. Actuators may be arranged on one or both sides of the movable members 420, as is illustrated in FIGS. 4b and 4c.

The actuators may be biased by bias springs 403 towards the movable member 420, and electrodes 404, 405 and 414 may be provided similar to what was disclosed in FIGS. 3 and 5a-5c.

Referring to FIG. 7c, the amplifying structure 412 may be designed to provide the gripping member 406 with a first movement component B1, e.g. by a bending movement of the amplifying structure. Furthermore, the amplifying structure 412 may be designed to provide the gripping member with a second movement component E1, e.g. by an extension movement of the amplifying structure 412.

By controlling the driving frequencies and/or phase applied to the electrodes 404, 405, advancing (R1, D1) or retreating (R2, D2) movement of the movable member 420 may be provided by combining out of phase B1 and D1 vibratory motions, wherein the phase shift between B1 and E1 and the magnitudes of B1 and E1 are functions of frequency. Those functions may be determined by the shape, fastening points and mechanical properties of the resonant horn.

To achieve a high force with the embodiment of FIGS. 7a-7c, the number of gripping members 406 should be maximized. In reality, manufacturing tolerances may limit the number of gripping members that can be provided at a commercially viable cost.

The configurations illustrated in FIGS. 6a-6b and 7a-7c enables a very thin actuator to be provided, while maintaining high force capability, as they allow as much active material as possible to be arranged in a low profile design. For example, the actuators illustrated in FIGS. 6a-6b and 7a-7c can be made as thin as 3-6 mm, while being 30-40 mm long, in the direction parallel with the body part. The actuator configuration in e.g. U.S. Pat. No. 6,870,304 cannot achieve this, since the vibration source therein is always configured in a transverse way to the pushing mechanism.

Hence, the actuators of U.S. Pat. No. 6,870,304 require a transmission mechanism, e.g. as described herein with respect to FIGS. 5a-5c.

FIGS. 8a-8b schematically illustrate an actuation unit 500 according to a fifth embodiment. In this embodiment, the actuation unit 500 comprises a housing 507, in which a resonant traveling wave rotary motor, a standing wave rotary motor, a displaced traveling wave motor, a general rotary ultrasonic motor or a similar motor 501 is arranged. Such motors are known to the skilled person. An output axis (not shown) of the motor 501 is connected via a transmission mechanism 518 to a spindle 509, arranged between spindle mounts 515a, 515b. The spindle may be arranged analogously to FIGS. 5a-5c.

The transmission mechanism of FIGS. 8a and 8b comprises a first gearwheel in contact with the output axis of the motor and a second gearwheel, which is in angular contact with the first gearwheel and connected to the spindle 509. Whereas gearwheels is one option, friction wheels may be another option for the transmission mechanism.

Depending on the direction of rotation of the motor 501 (R1 or R2), the compression member 520 may be wound on (D1) or off (D2) the spindle. The rotation direction and speed of the motor may be controlled by phase between excited rotor sections, i.e. traveling wave speed.

The motors referred to in connection with FIG. 8a-8b can also be mounted directly on the spindle axis, provided that sufficiently high torque may be provided.

For a further description of ultrasonic motors, reference is made to Toshiiku, S., Kenjo T.: *An Introduction to Ultrasonic Motors*, Clarendon Press, Oxford, 1993.

Figure 9:
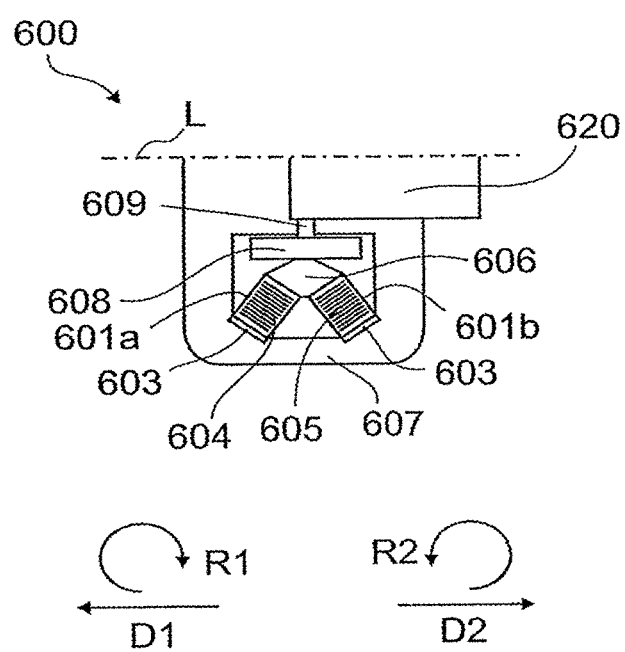
FIG. 9 schematically illustrates part of an actuation device according to a sixth embodiment.

FIG. 9 schematically illustrates part of an actuation unit 600 according to a sixth embodiment. In this embodiment, which is similar to the one described with reference to FIGS. 5a-5c, a pair of separate actuators 601a, 601b are arranged at an inclined, preferably acute, angle to a wheel 608, one actuator for each direction. The wheel 608, in its turn, is connected to a spindle 609, upon which the compression member 620, or a connection member connected thereto, may be wound. Thus, by activating a first actuator 601a, the gripping member 606 will move in the direction indicated by reference numeral R1, whereby the compression member 620 will move in the direction indicated by reference numeral D1. Oppositely, by driving the second actuator 601b, the gripping member 606 will move in the opposite direction R2 and the compression member 620 will move in the opposite direction D2. Alternatively, the actuators may be driven together with a phase difference to provide similar effects. The actuators, which may each be provided with a stack configuration or as bulk actuators, may be driven at their respective 1st longitudinal resonance or anti-resonance frequency.

The actuators 601a, 601b may be mounted relative to the housing 607 using elastic mounts 603.

The actuators may also comprise multiple electrode sets, such that a combination of bending and longitudinal vibration can be established in each actuator. This allows for a more controlled elliptical motion to be produced by the gripping member.

FIGS. 10a-10d schematically illustrate an actuation unit 700 according to a seventh embodiment. In this embodiment, the actuation unit 700 comprises a housing 707a, 707b, through, or into, which a compression member 720, or a connection member connected thereto, is slidable. The compression member 720 may be provided with a ratchet structure 722, comprising at least two, preferably a plurality of, locking surfaces 722a and a substantially corresponding number of ramp surfaces 722b. The locking surfaces 722a may all face the same direction, typically the direction D2 in which the locking effect is to be achieved.

An actuator, which may comprise first and second actuator sections 701a, 701b, may be arranged on one, or both, faces of the compression member 720. A first actuator section 701a may have an elongate cross section forming an acute angle relative to the compression member 720, and may be extendible upon activation, so as to engage the locking surface 722a, thereby pushing the compression member 720 in the direction indicated by reference numeral D1. The outermost part of the actuator may form a gripping member 706 adapted for interaction with the ratchet structure 722.

The actuator 701a, 701b and the compression member 720 may be biased towards each other by biasing springs 703a, 703b.

The second actuator section 701b, which is optional, may be arranged to bend the actuator, such that the gripping member 706 is moved away from the engagement with the ratchet structure 722.

Figure 10A:
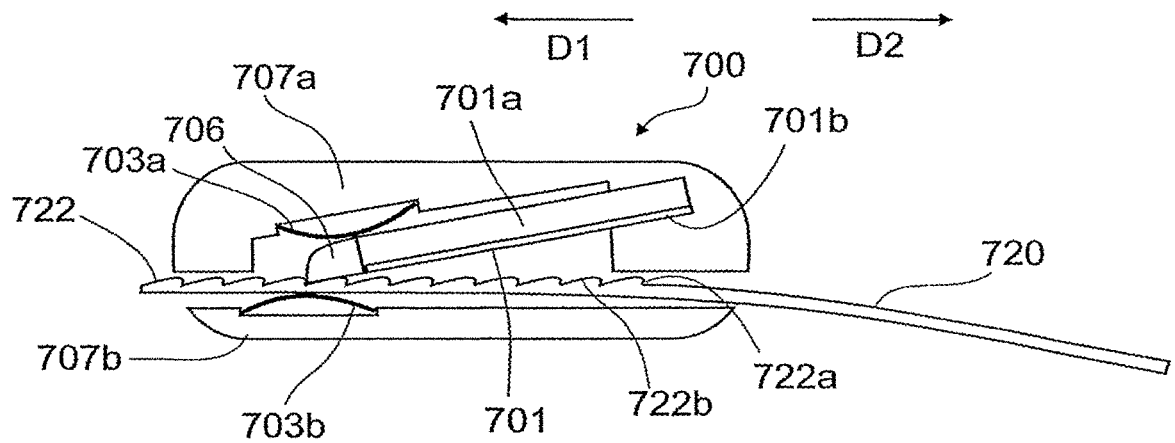
FIGS. 10a-10d schematically illustrate an actuation unit according to a seventh embodiment.
Figure 10B:
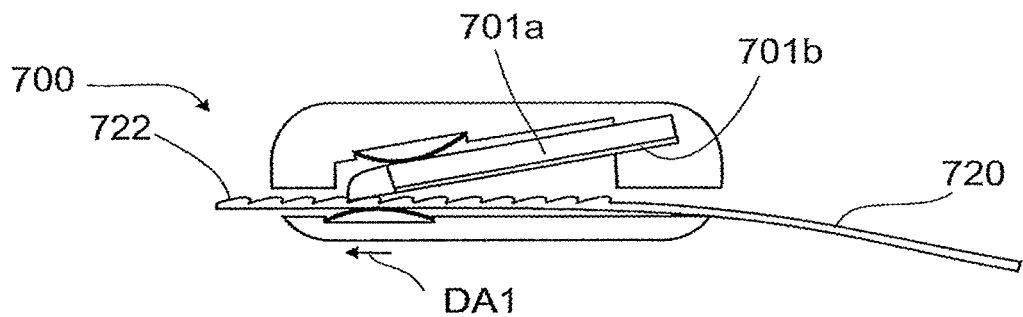
Figure 10C:
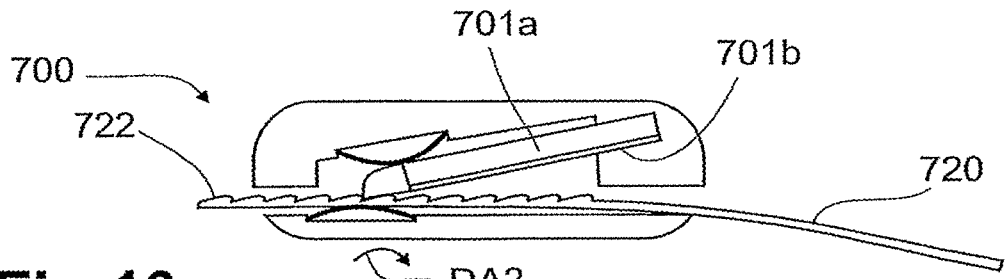
Figure 10D:
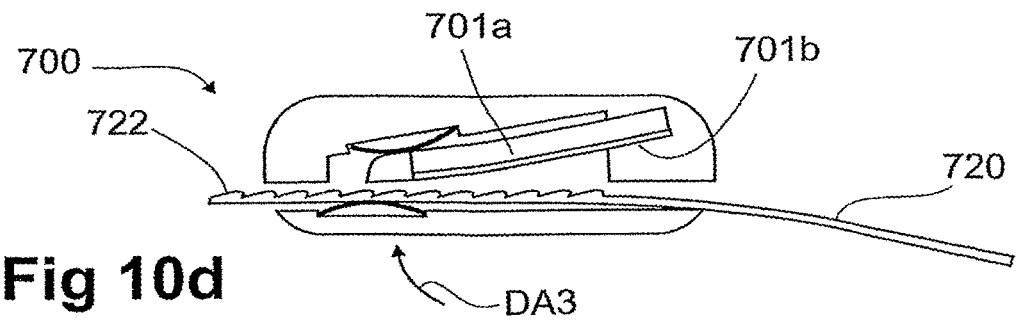

FIGS. 10b-10d illustrate a movement sequence of the actuation unit 700 illustrated in FIG. 10a.

In a first phase, illustrated in FIG. 10b, the first actuator section 701a is extended, preferably slowly, while in contact with a locking surface of the ratchet structure 722, so as to move the ratchet structure 722 and the compression member 720 in the direction DA1.

In a second phase, illustrated in FIG. 10c, the first actuator section 701a is contracted at a speed higher than the extension speed in the first phase, so as to engage the locking surface to the right of the locking surface engaged in the first phase. Hence, the gripping member will move as indicated by the arrow DA2. Typically, the speed of this phase must be higher than the first natural mode of the system created by the body part and the compression member.

Typically, the maximum step time for this second phase must be less than the associated response time of the system created by the compression member and the body part. For applications where the compression member is reasonably stiff in comparison to the body part, the elastic recovery of the body part will determine the slowest allowable step time. In applications where the compression member is reasonably soft in comparison to the body part, the elastic recovery of the compression member will determine the slowest allowable step time.

Preferably the step time for this phase may be 5% or less than the recovery time for the system created by the compression member and the body part to ensure suitable compression dynamics and overall efficiency.

The first and second phases are repeated to macroscopically advance the compression member 720 in the D1 direction.

In a third phase, illustrated in FIG. 10d, the second actuator 701b is activated, so as to cause the gripping member to move away from the ratchet structure 722, thereby allowing a free movement of the compression member also in the D2 direction. The gripping member will thereby move in the direction indicated by the arrow DA3. The first and second actuator sections may be arranged as a bi-layer structure, whereby a bending movement is achievable by actuation of the second actuator section 701b. The movements of the first and second actuator sections can be coordinated to reduce stresses on the sections and boost performance. Such coordinated movement of actuator sections 701a and 701b can also smooth out operation of the device thereby extending component lifetime, reducing step vibration transmission to the housing or reducing audible noise.

The rapid return of the second phase may be provided in different ways depending on the type of actuator used. E-field activated materials may be short-circuited. Conducting polymers may be subjected to rapid reverse voltage and temperature activated memory alloys may be rapidly heated.

The ratchet structure 722 may be nano or meso scale and molded directly into the compression member or the connection member. The ratchet structure provides for rectification and high force capability.

The actuators described with respect to FIGS. 10a-10d may take larger steps than the ones previously described, typically from about 100 micron to about 1 mm or more. They also require more active material or larger energy density materials. Although such embodiments may require more active material, or larger energy density materials, than previous examples to achieve similar power output, they have some significant advantages over resonant drive approaches, such as longer life of the gripping member and connecting member, lower operating stresses at the gripping member (allowing for higher friction material selection such as polymers and elastomers), quieter operation (can be driven at less than 20 kHz), lower manufacturing tolerance requirements, more control of the gripping member movement and potentially higher holding force due to the ability to use strong interlocking surfaces between the gripping member and the connecting member.

A pair of coordinated actuation units such as the one described in FIGS. 10a-10d may be arranged to provide a coordinated stepping engagement.

Figure 11:
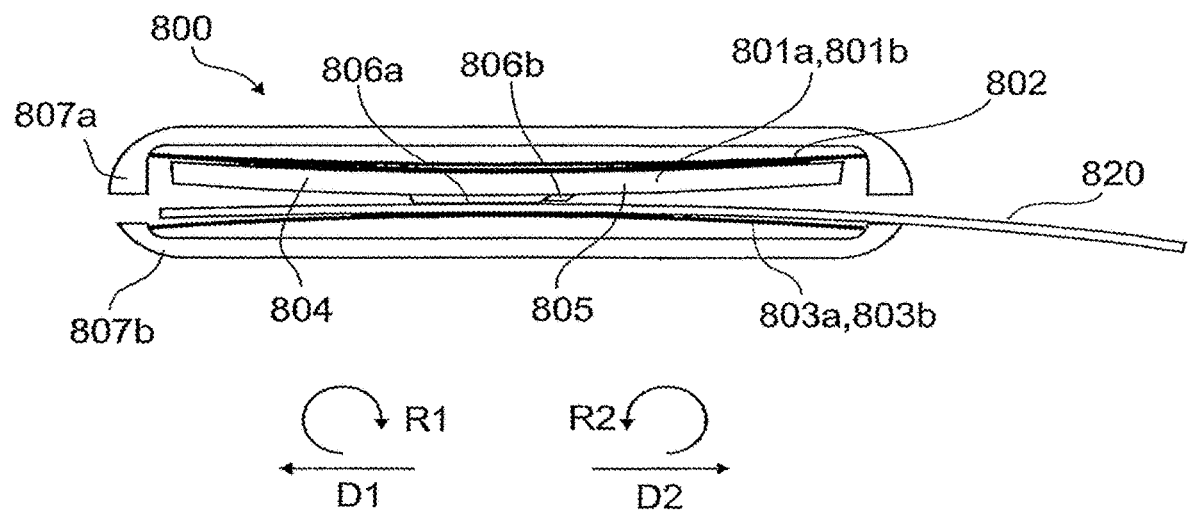
FIG. 11 schematically illustrates an actuation unit according to an eight embodiment.
Figure 12:
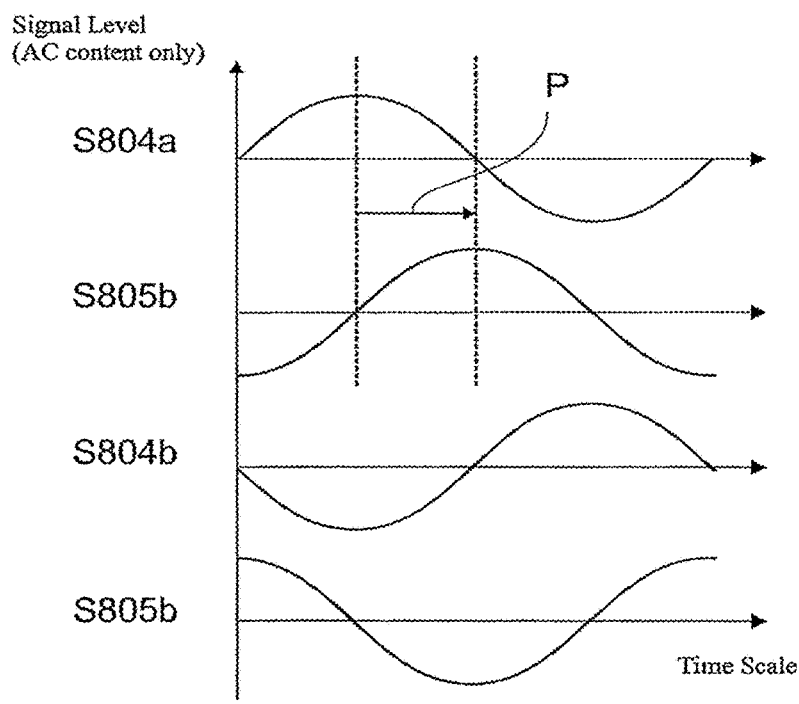
FIG. 12 schematically illustrates drive signals for the actuation unit of FIG. 11.

FIG. 11 schematically illustrates an actuation unit 800 according to an eighth embodiment. FIG. 12 schematically illustrates drive signals for the actuation units of FIG. 11. This embodiment is similar to the one described with respect to FIG. 3 for applications requiring higher pulling force. The actuation unit 800 comprises a flexible substrate 802 is arranged in an upper housing 807a and carries two or more actuators 801a, 801b, which are individually drivable. Gripping members 806a, 806b protrude from the respective actuator towards the movable member 820, which may be a compression member or a connection part connected thereto.

Bias springs 803a, 803b may be provided in a lower housing 807b for biasing the movable member 820 towards the gripping members 806a, 806b. Additional biasing may be provided by the flexible substrate 802.

In an alternative arrangement, the bias springs 803a, 803b can be replaced with another group of actuators. The operation is similar to the case with bias springs, except that higher forces can be realized. In such a situation, opposing actuators, positioned opposite the compression member 820, would be driven in phase with each other such that each pair of opposing actuators, or opposing gripping members, will act to grip and release the compression member 820. In addition, in such an alternative embodiment, the compression member 820 may be provided with a ratchet-like texture on both of its actuator facing surfaces.

In this embodiment, the actuators 801a, 801b may be drivable with a phase lag or delay P, for example as indicated by FIG. 12, which indicates the signals $S_{804a}$, $S_{805a}$, $S_{804b}$, $S_{805b}$ to the respective electrode set 804a, 805a, 805a, 805b of the respective actuator 801a, 801b

By activating the first electrode set 804a, 804b of the respective actuator 801a, 801b, a gripping member movement corresponding to reference numeral R1 may be provided, resulting in a tightening movement D1 of the movable member 820.

By activating the second electrode set 805a, 805b of the respective actuator 801a, 801b, a gripping member movement corresponding to reference numeral R2 may be provided, resulting in a releasing movement D2 of the movable member 820.

Hence, the actuators may be controlled such that at any point in time, at least one of the gripping members 806a, 806b is in force transferring contact with the movable member 820. Thus, the gripping members 806a, 806b may "walk" on the movable member 820.

The gripping members 806a, 806b may be asymmetric, microribbed or V-shaped, as indicated in FIGS. 25a-25b, 26a-26e, 27a-27l or 28a-28f. Also, the movable member 820 may be provided with a microribbed structure for interaction with the structure of the gripping member 806a, 806b. Alternatively, static friction can be relied on for generating a static holding force.

The actuation units themselves can be built in an asymmetrical way such that the pulling force and return force are tailored to the requirements of the compression application. Compression applications in general do not require high return force, so by utilizing the majority of the active material in the pulling phase of the compression, one can maximize the pulling force while minimizing the amount of active material and still maintaining reasonable movement for the return stroke (at lower force levels).

High force capability is obtained by the coordinated stepping movement, whereby one gripping member always contacts the movable member. Also, the provision of a high strength flexible substrate 102 increases the force capability by providing support for the active material, better acoustic quality and higher fatigue strength, allowing a larger biasing force between the gripping member and the movable member, without damaging the active material. This also allows for shaping the vibration waves for resonant operation.

The combination of the static friction properties of the interface and the bias force can also be used as a configurable mechanical fuse. If the external force exceeds the maximum force sustainable at the interface between the gripping member and the compression member, it will start to slip. This mechanical fuse can be used to provide an extra level of mechanical safety for the user and/or as a means of protecting the internal components of the actuator units.

FIGS. 13a-13c schematically illustrate an actuation unit 900 according to a ninth embodiment. In this embodiment, the movable member, i.e. compression members 920a, 920b, or connection members connected thereto, are provided with a ratchet structure or a series of perforations 922.

The gripping member 906 may take the form of a hook extending from a base fixture 921, the hook being bendable and expandable/contractable by respective actuators 901a, 901b. Hence, the actuators comprise bending actuators for controlling the gripping member between a gripping position and a non-gripping (or repositioning) position; and extension actuators for providing the pulling motion or re-positioning motion. At the outer portion of the gripping member, a hook or other type of positive interlocking device is formed for interaction with the ratchet structure or perforations 922.

The ratchet structure may extend in a direction parallel with the movable member's direction of motion, and may comprise at least two, possibly three or more parallel ratchet structures.

The gripping members may be arranged to be driven with a delay between their respective cyclic motions, such that, at any point in time, at least one of the gripping members is in force-transferring engagement with its associated ratchet structure. For example, the actuators controlling the extension of the gripping members may be driven at a 180 degree phase delay, whereas the actuators controlling the bending of the gripping members may be driven at a 90 degree phase delay. Preferably, shaped (i.e. non-sinusoidal) wave forms are used. Hence, there is always a positive clamping of the movable member. Thus, referring to FIG. 13c, a pair of gripping members 906 engaging a movable member 920a on one side of the actuation unit 900 may perform the movements indicated by R1 and R1', wherein R1 and R1' may be delayed 180 degrees, i.e. half a period. Similarly, gripping members 906 on the other side of the actuation unit 900 may perform similar movements. In FIG. 13c, a retreating movement is indicated by R2 and R2', wherein R2 and R2' may be delayed 180 degrees, i.e. half a period.

The gripping members 906 may be arranged within an interior space of a housing 907a, 907b. An electrolyte for electrochemically activated polymer actuators may be arranged in the space. In addition, a counter electrode may be printed along the interior walls of the guide member 907a, 907b.

It is recognized that the actuation unit of FIGS. 13a-13c can be provided as double sided or single sided, i.e. operating on one or two movable members 920a, 920b.

The positive gripping provided by the actuation unit 900 enhances force capability.

An alternative in this case is that the gripping member 906 is simply a passive piece that is formed onto or out of the outermost tip of the actuator 901. In this sense, it could be a hook-like structure that is bonded to the actuator but it could also be a piece that is punched or pressed out from a passive material at the end of the actuator. The gripping member may also be the flexible substrate onto which the actuators are manufactured and the tip could either be a molded member of that substrate, or deposited separately onto the substrate during manufacture.

The actuation unit of FIGS. 13a-13c is most amendable to polymer and memory alloy type active materials as the lack of pre-compression and the requirement for tensile forces negates the use of ceramic type active materials, which may crack when subjected to tensile stresses. The ratcheting mechanism of the compression member accommodates natural creep of the actuators through their number and spacing.

FIGS. 14a-14g schematically illustrate an actuation unit 1000 according to a tenth embodiment. This actuation unit comprises a movable member 1020, connected to a first compression member and a guide member 1023 connected to another compression member 20, which may extend in a direction opposite to the first connection member. The guide member may comprise a channel or other tubular structure, having an arbitrary cross section, and extending substantially parallel with an intended direction of movement of the movable member, whereby the gripping member is movable inside the channel or tubular structure.

A gripping member, connected to the movable member 1020, comprises first and second longitudinally spaced-apart clamp members 1006a, 1006b, which are controllable for releasable engagement with the guide member 1023.

In the embodiment illustrated in FIGS. 14a-14g, the clamp members 1006a, 1006b may be individually controllably expandable and contractable in a direction transverse of the direction of movement, so that the clamp members 1006a, 1006b may engage the guide member, e.g. inner walls of a channel, to lock the gripping member relative to the movable member.

The gripping member may further comprise a longitudinal movement member 1006c extending between the clamp members. The longitudinal movement member 1006c may be controllably expandable and contractable in a direction parallel with direction of movement.

Cables 1024 for controlling the clamp members 1006a, 1006b and the longitudinal movement member 1006c may be included in the structure.

Alternatively, the guide member may comprise a track or guide rail, whereby the clamp members wholly or partially encircles the track or guide rail.

Figure 14A:
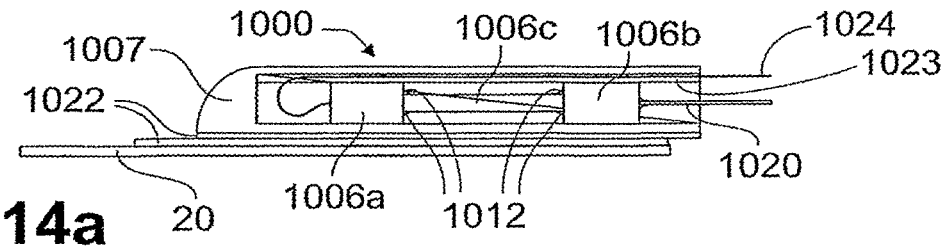
FIGS. 14a-14g schematically illustrate an actuation unit according to a tenth embodiment.

The actuation unit 1000 of FIG. 14a can provide high force capability by provision of a textured surface on the clamping members and on the guide member. Such texturing can easily be implemented as a final step in the manufacture of monolithic actuator units. Texturing may also be applied to the clamp member facing surfaces of the guide member. Force capability is improved by the fact that there is always one clamp member maintaining contact with the guide member.

Figure 14B:
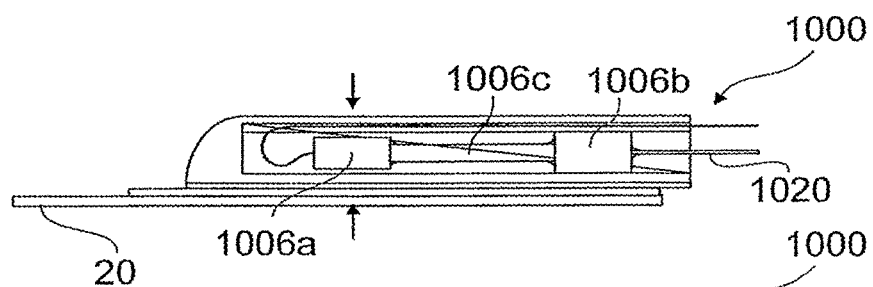
Figure 14C:
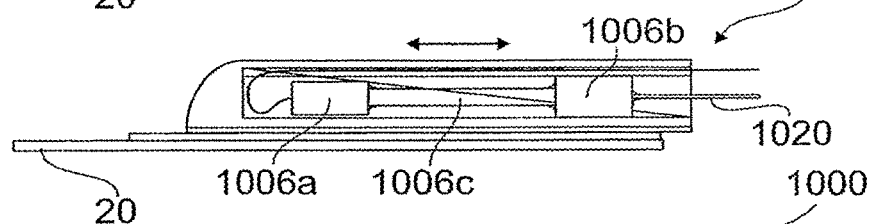
Figure 14D:
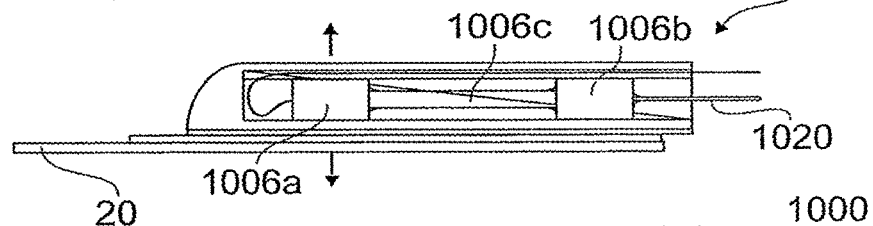
Figure 14E:
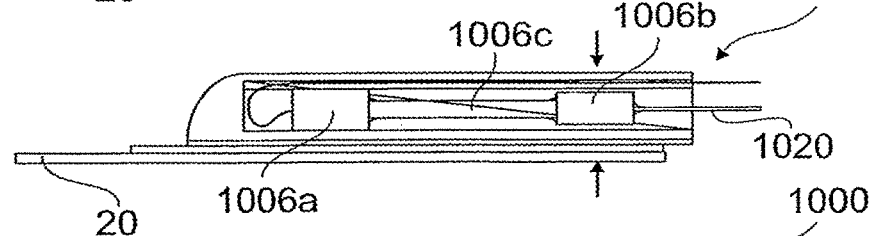
Figure 14F:
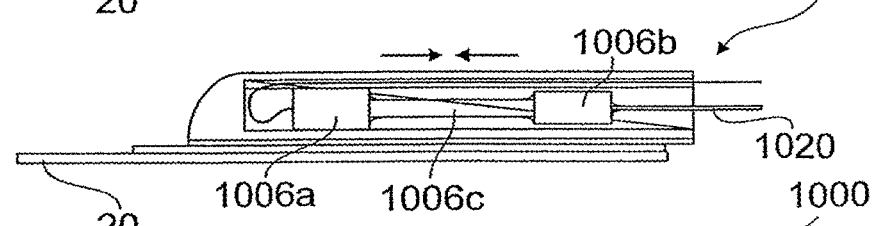
Figure 14G:
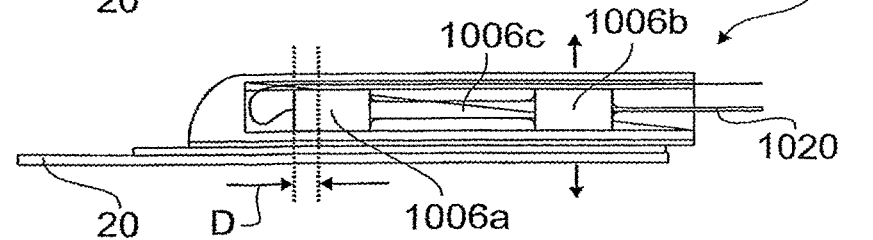

The actuation unit 1000 may be operated as follows:

Referring to FIG. 14b, a first clamp member 1006a may be disengaged, while the second clamp member 1006b is engaged. Referring to FIG. 14c, the longitudinal movement member 1006c is elongated. The second clamp member 1006b remains engaged. Referring to FIG. 14d, the first clamp member 1006a is engaged. The second clamp member 1006b remains engaged. Referring to FIG. 14e, the second clamp member 1006 is disengaged, while the first clamp member 1006a is engaged. Referring to FIG. 14f, the longitudinal movement member 1006c contracts. The first clamp member 1006a remains engaged. Referring to FIG. 14g, both clamp members 1006a, 1006b are engaged, whereby the actuator has moved a distance D, as indicated in the figure.

Using the principles outlined with respect to FIG. 14a-14g, it is possible to provide locking upon power removal. Static friction between the guide member and the clamp members may be used, or alternatively, ratchet structures may be provided on the guide member and/or the clamp members. It is also possible to provide this arrangement relatively silent, using polymer actuators or ceramic ones.

In the case that the longitudinal member is of a constricting type (constricts during activation rather than expands as depicted in FIGS. 14b-g), then the sequence of operation for the clamping members is to be reversed from that shown in FIGS. 14b-g.

It is preferable that the actuator 1006a, 1006b, 1006c is constructed as a monolithic block. In that way, electrode sets for the longitudinal movement member 1006c and the first and second clamping members 1006a, 1006b can be printed automatically during the actuator layering process. A monolithic block also requires less reinforcements at the fastening points 1012 as such connections are made automatically as a result of the manufacturing process.

The embodiment of FIGS. 14a-14g is not very well suited to ceramic type longitudinal actuators without alterations to the clamp members. The reason for this is that generally, ceramic type actuators operating in longitudinal mode cannot provide sufficient stroke to disengage the guide member without strict manufacturing tolerances. In the case of a ceramic type actuator, the clamp members could be bimorph in nature to generate sufficient stoke length so as to disengage the guide member during operation.

As an alternative to ceramic type actuators, single crystal actuators can achieve sufficient stroke in a longitudinal mode such that the clamping members can engage and disengage the guide member.

The approach of FIGS. 14a-14g is quite amendable to polymer actuators in general. In the case of electrochemically activated polymer actuators, the space around actuator 1006 would be filled with a suitable electrolyte. A counter electrode can be printed on the inside surface of the guide member and perforations or longitudinal trenches could be formed on the longitudinal member so as to facilitate rapid ingress and egress of ions from the electrolyte into the polymer and vice versa during operation. The detailed design of such trenches is best facilitated by computer simulation and experimental validation to determine ultimate operating speeds, stresses and pulling capabilities for a particular design.

The surfaces of the clamping actuators 1006a and/or 1006b or the channel with which they interface may be modeled so as to have micro-formed ridges as per FIGS. 24-28 so as to increase the gripping force that they can apply to the housing track. Therefore the gripping force of the actuator can be increased beyond that available from simple smooth track and clamp surfaces. The spacing of such a ratchet pattern must be less than the maximum stroke length of the primary actuator section 1006c.

Figure 15A:
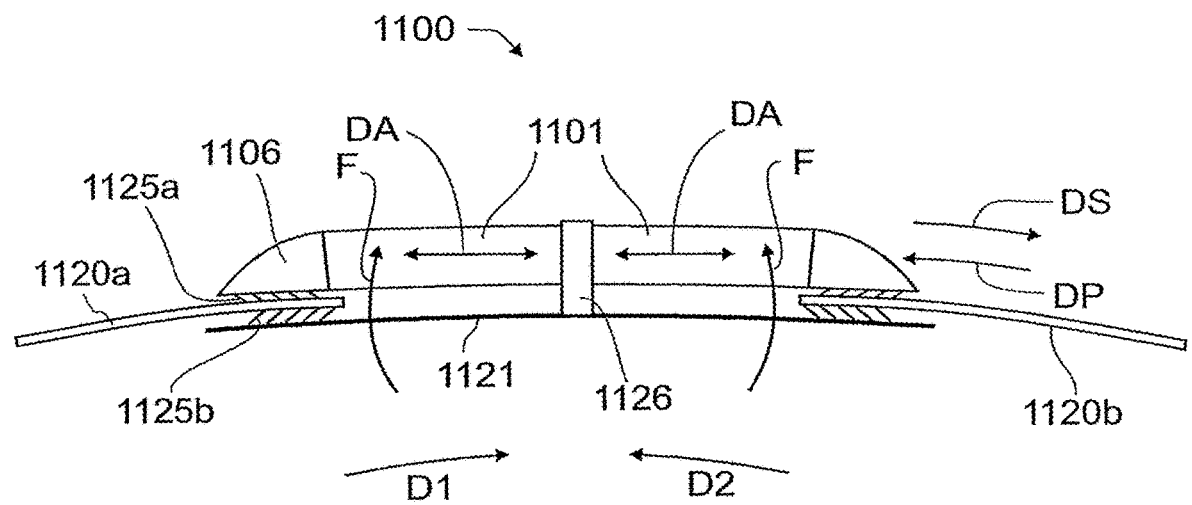
FIGS. 15a-15b schematically illustrate an actuation unit according to an eleventh embodiment.
Figure 15B:
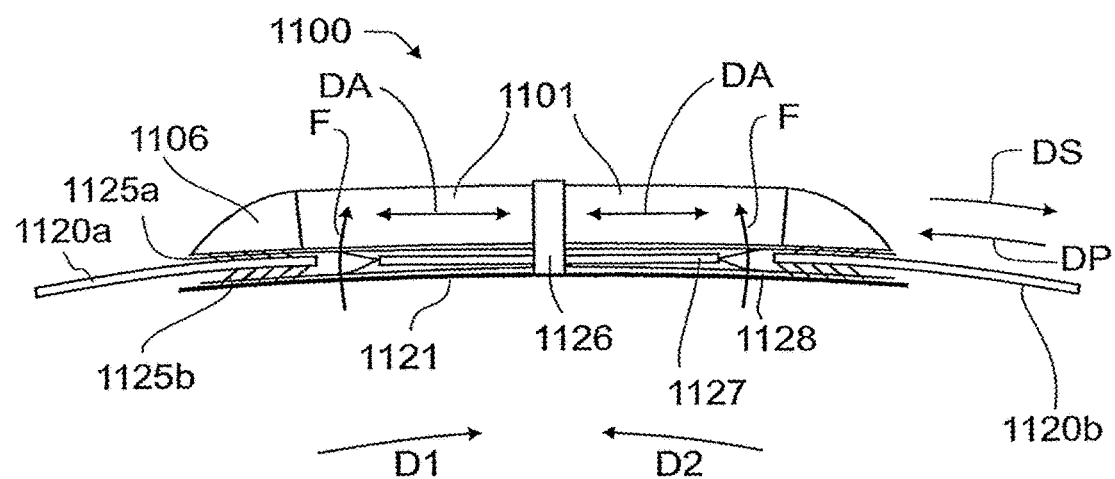

FIGS. 15a-15b schematically illustrate an actuation unit 1100 according to an eleventh embodiment. In this embodiment, the actuator 1101, attached to a mounting harness 1126, may be arranged to cause the gripping member 1106 to perform a reciprocating motion, having a component in a plane substantially parallel with an intended direction of movement D1 of the movable member 1120a, 1120b. The movable member 1120a, 1120b may be clamped between two actuators 1101 or between an actuator 1101 and a mounting base 1121, as illustrated in FIGS. 15a-15b.

Between the gripping member 1106 and the movable member 1120a, 1120b, there may be provided a rectification device 1125a, 1125b providing a high friction between the gripping member 1106 and the movable member 1120a, 1120b during a first part of the reciprocating motion, wherein the gripping member moves in a first direction (DP) in the plane, and providing low friction between the gripping member 1106 and the movable member 1120a, 1120b during a second part (DS) of said reciprocating motion, wherein the gripping member moves in a second, opposite direction. Thus, during the first part (DP) of a stroke, the rectification device will cause the movable member 1120a, 1120b to follow the gripping member's 1106 motion, whereas during the second part of the stroke, the rectification device will allow the movable member 1102a, 1120b to slip relative to the gripping member 1106. The mounting base and the actuators may be lightly biased towards each other.

Such rectifying devices may be arranged also between the mounting base 1121 and the movable member.

As an example of a rectifying device, inclined or asymmetric or inclined microfilaments may be mentioned. Non-limiting examples include plastic or metallic needle filaments. Inclined lips or ridges may also be provided. The actuator needs to move more than the engagement/disengagement distance of the rectifying device, to ensure a positive net movement.

Particularly suitable actuator materials comprise electroactive polymers of either ferroelectric or conducting polymer classification, shape memory alloys or piezoelectric crystals or ceramics. Piezoelectric versions may require bias springs to be provided as illustrated in e.g. FIG. 3. Polymer versions could include rolled actuators or actuator arrays or multilayered actuators, with the layering being parallel to the movable member.

The actuator could be a single actuator mounted on the mounting harness. Alternatively, the mounting harness, mounting base and actuator may be molded or otherwise constructed together.

The biasing force F, clamping the movable member 1120a, 1120b between the gripping member and the mounting base 1121 may be applied in a per se known manner.

The actuation unit 1100 illustrated in FIG. 15a may be a one-way device, without capability of providing a controlled release of the movable members 1120a, 1120b.

As is illustrated in FIG. 15b, the actuation unit 1100 of FIG. 15a may be modified into an actuation unit 1100', which is capable of controlled release of the movable members 1120a, 1120b. This may be achieved by providing a device 1127, 1128, e.g. a tweezer mechanism, which upon actuation causes the rectification device 1125a, 1125b to at least partially disengage from the movable members 1120a, 1120b, thereby allowing movement in any direction, including a releasing movement. Such a tweezer mechanism may alleviate the biasing force F and/or act so as to separate the actuator 1101 from the mounting base 1121.

Another option for allowing disengagement could be to allow the gripping member to move away from the movable member, e.g. by a folding mechanism.

Alternatively, the rectification device could be provided on the movable member 1120a, 1120b, instead of on the gripping member and on the mounting base 1121.

In another option, the microfilaments of the rectification device 1125a, 1125b could be constructed from active material bending actuators. Upon activation, they can retract into the gripping member 1106 and the flexible base 1121 thereby disengaging the actuator 1101 from the movable members 1120a, 1120b. The motion of the active material microfilaments and the actuators could be coordinated in the event that one wanted a controlled retreat of the movable member.

The force capabilities of this design are determined by the ratio of the engage/disengage distance of the rectification mechanism and the stroke length of the actuators, and the force capabilities of the actuators. As there is no need for a direct biasing mechanism, suitable engagement can be attained with a light bias, the efficiency of this actuation mechanism can be very high.

Furthermore the rectifying means may comprise a ratchet structure arranged for interaction with said inclined microfilaments. Such a ratchet structure may be arranged on the surface or surfaces facing the microfilaments to provide positive interlocking by interaction with the microfilaments.

Figure 16:
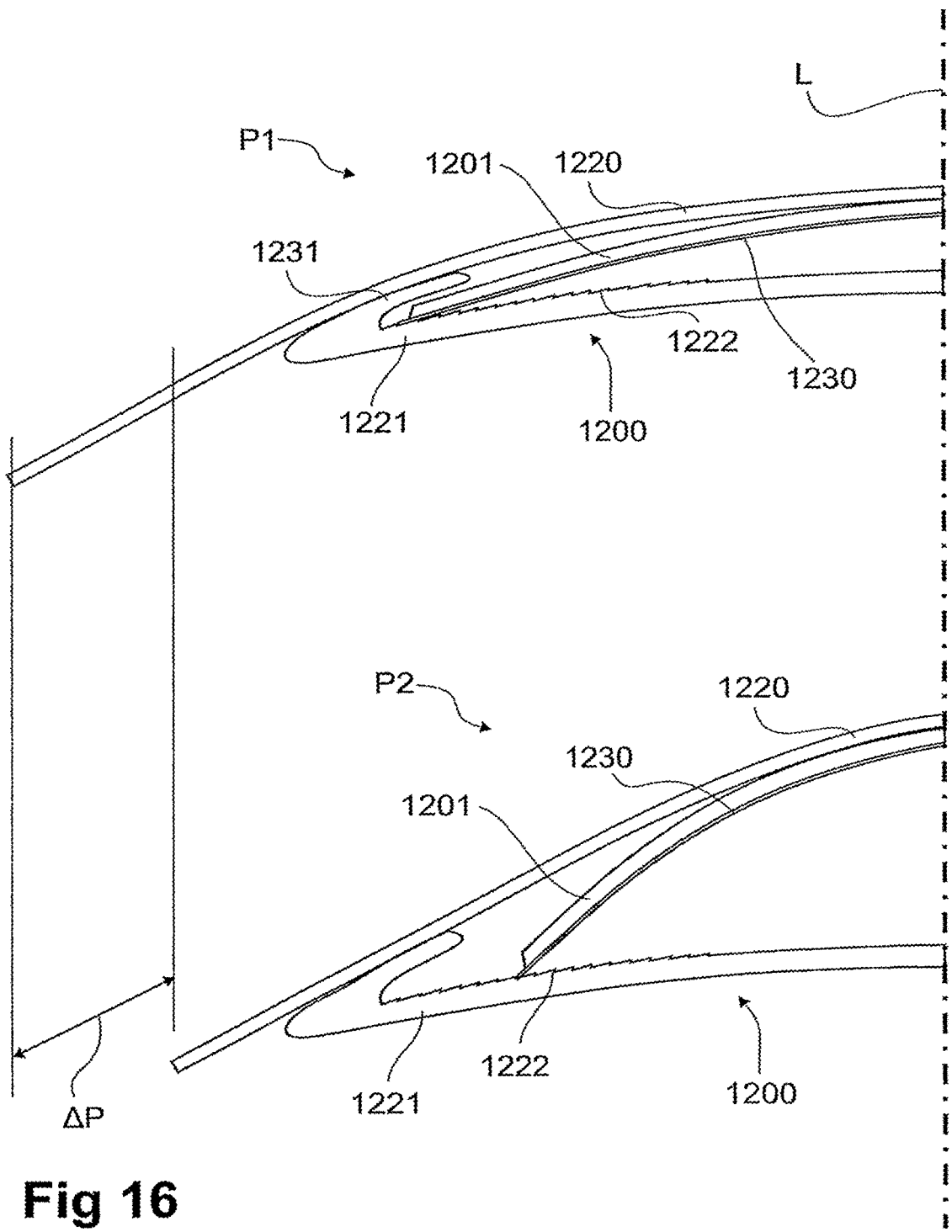
FIG. 16 schematically illustrates an actuation unit according to a twelfth embodiment.

FIG. 16 schematically illustrates an actuation unit 1200 according to a twelfth embodiment, wherein the actuation unit 1200 is arranged to control a radial. distance DR (FIG. 4) between the body part 2 and the movable member (compression member 1220, or a connection member connected to the compression member). In this embodiment, the compression member encircles the body part and the actuation unit is arranged between the body part and the compression member. When activated, the actuation unit locally pushes the compression member away from the body part, thereby effectively tightening the compression member.

The actuation unit may comprise a mounting base 1221, extending between two circumferentially spaced apart portions of the movable member 1220. A controllably bendable actuator element 1201 may be provided to control a radial distance DR, along the line L of symmetry, between the mounting base 1221 and the movable member 1220. A central portion of the actuator element 1201 may bear against an inside of the movable member 1220, whereas the edges or tips of the actuator element 1201 may interact with a ratchet structure 1222 arranged on or integrated with the mounting base. The actuator 1201 may be supplemented by a spring 1230, which may be suitably biased towards the tightened (P2) or towards the released position (P1). There may also be provided a spring element 1231 at the outermost edge of the mounting base 1221, this outermost spring element being arranged to provide a force having a radial component towards the movable member 1220. Such a spring element may improve force transmission to deformation ratio to further improve performance.

The actuation unit 1200 of FIG. 16 may operate as follows. In the loosened position P1 shown in the upper part of FIG. 16, the edge of the actuator element 1201 is in engagement with an outermost portion of the ratchet structure 1222. By activating the actuator element 1221, it bends, together with the spring 1230, thereby causing its central portion to move away from the mounting base 1221 in a radial direction, along the line of symmetry L. While bending, the edge of the actuator element shifts along the ratchet structure 1222, which may prevent it from moving backwards.

Turning to the lower portion of FIG. 16, which shows the actuation unit 1200 in its tightened position P2, it is noted that a net tightening effect ΔP is achieved.

The embodiment of FIG. 16 may either operate as a hopping actuator, or two actuators 1201 may be arranged in parallel and be individually controllable. This process can also be reversed for releasing the compression member.

Alternatively, to release the actuation unit 1200 of FIG. 16, a reversed hopping movement may be used, or a separate disengagement mechanism may be provided.

For example, controlled retreat of the actuation unit can be achieved by using an actuator with multiple configured electrode sets. Coordinated activation of both electrode sets can create elliptical motion at the contact point between the actuator 1201 and the ratchet structure 1222 that has either a clockwise or counterclockwise direction sense. The motion of this embodiment, in general, would be similar to that as described in FIG. 10*b-d* for an inertial (hopping) configuration.

This approach may be very useful for active materials that require pre-compression, such as ceramics. It may also be useful for some polymer actuators to bond them to the flexible substrate in a stretched state so as to maintain the property enhancements that are achieved through such stretching. An example is ferroelectric polymers, wherein the dielectric breakdown strength is significantly increased as the polymer chains align during such pre-stretching.

Figure 17:
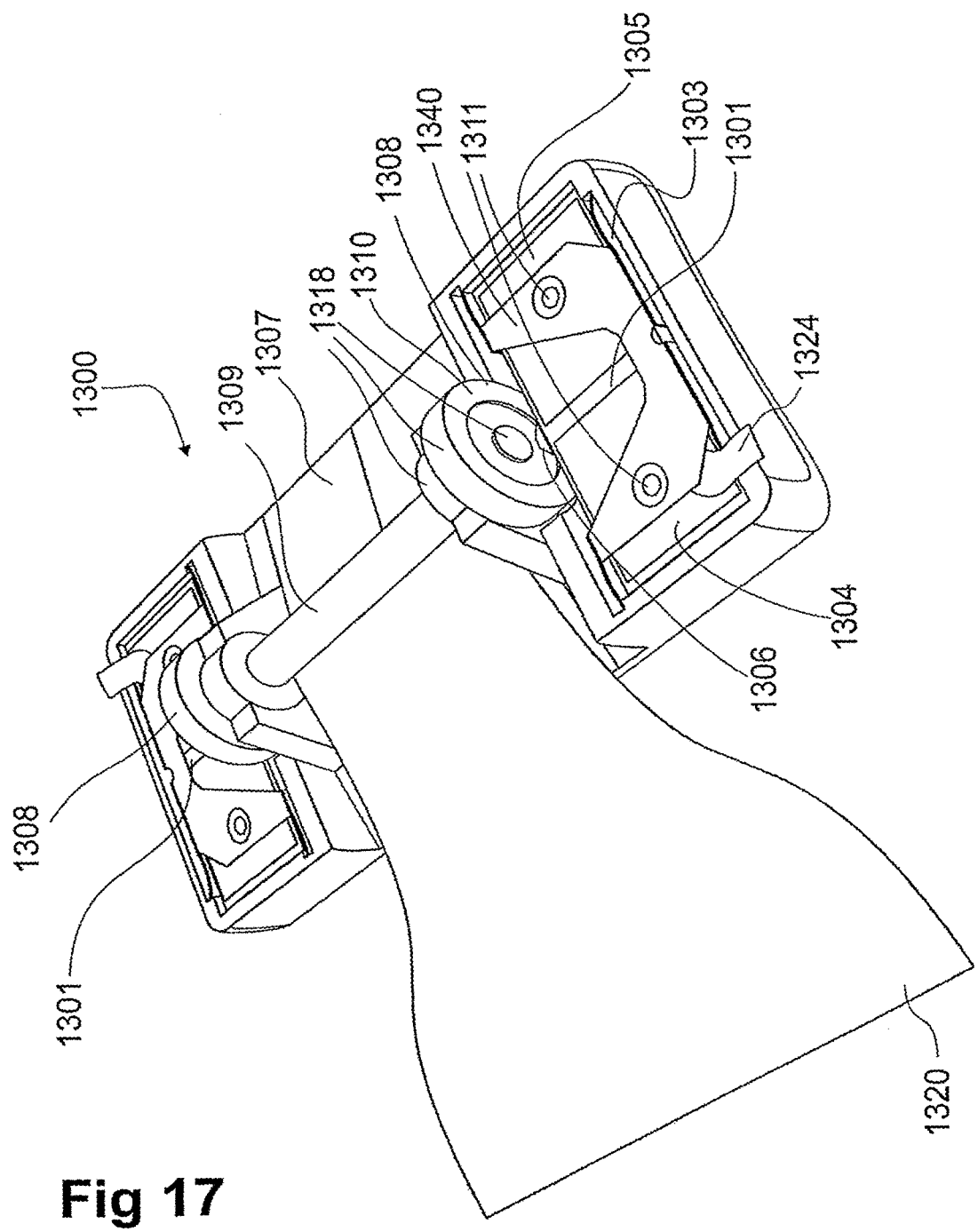
FIG. 17 schematically illustrates an actuation unit according to a thirteenth embodiment.

FIG. 17 schematically illustrates an actuation unit 1300 according to a thirteenth embodiment, which is a possible practical application of the embodiments disclosed in FIGS. 5*a*-5*c* or 9. The actuation unit 1300 of FIG. 17 comprises a housing 1307 having one or two openings for a movable member 1320. Only one movable member is shown in FIG. 17, but it is recognized that two or more members may be provided. Actuator arrangements comprising respective actuators 1301, bias springs 1303, electrode sets 1304, 1305 and gripping members 1306 are indicated. The actuator 1301 may be mounted by mounting points 1311 in a mounting bracket 1340. A spindle 1309 is provided at a central portion of the actuation unit 1300, extending between respective wheels 1308 having respective contact surfaces 1310 for interaction with the respective gripping member 1306.

Hence, the wheels 1308 form a transmission mechanism 1318 from the gripping member 1306 to the spindle 1309.

In the embodiment of FIG. 17, a high force capability can be provided by the active material portion of the actuator being fixed relative to the mounting bracket 1340 only at its nodes (points or lines of minimal vibration), i.e. the mounting points 1311 coincide with the nodes of the excited active material portion. This provides maximum vibration velocity and alleviates manufacturing tolerances on the housing. Also, the mounting bracket 1340 may be a flexible harness, which may be biased towards the wheel 1308.

Figure 18:
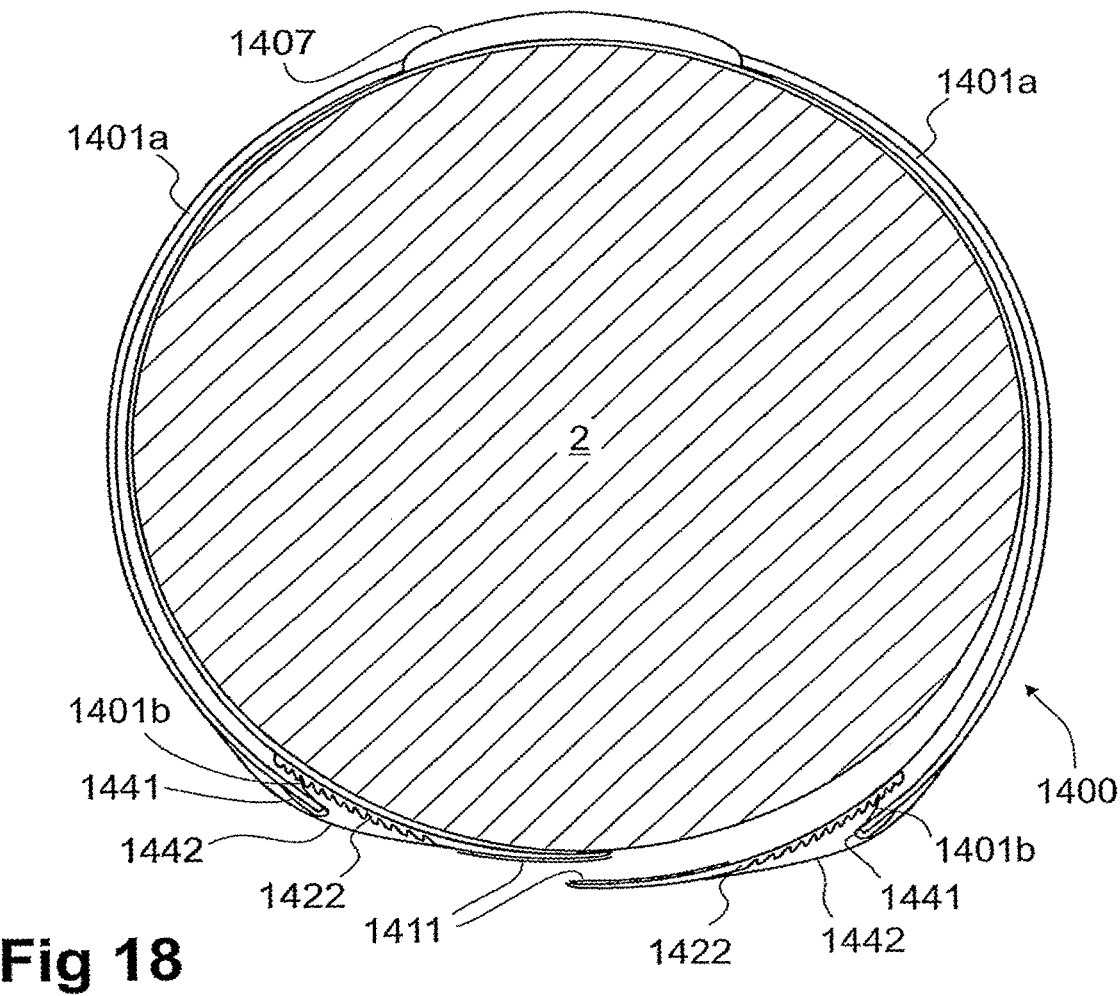
FIG. 18 schematically illustrates an actuation unit according to a fourteenth embodiment.

FIG. 18 schematically illustrates an actuation unit 1400 according to a fourteenth embodiment. In this embodiment, each primary actuation unit 1401*a* partially encircles the body part 2. The primary actuation unit 1401 is arranged to provide a stepwise compressive force to the body part 2, by interaction between a ratchet structure 1422 and gripping member 1406 connected to the primary actuator 1401*a*. The embodiment illustrated in FIG. 18 may operate in a manner similar to what has been described with respect to FIGS. 11 and 13*a*-13*c*, i.e. having coordinated gripping members operating in parallel, such that there is always one gripping member engaging the ratchet structure, while the other gripping member moves relative to the ratchet structure.

The fact that there is always one gripping member engaging the ratchet structure, provides for high force capability.

Also, by arranging the device of FIGS. 18-20 to pull only in its passive state and to expand in its active state, the device will self lock when no power is applied to it, thereby reducing power consumption.

The primary actuator 1401*a* may be expandable and contractable in a circumferential direction, i.e. it is variable in length and wrapped around the body part. At a first end or edge, the primary actuator 1401*a* may be attached to a housing 1407, which may contain electronics and connectors etc. At a second end or edge, the primary actuator 1401*a* engages the ratchet structure 1422. Between the respective primary actuator 1401*a* and the body part, there may be an inner layer 1445, which at one end or edge is attached to the housing 1407, and at a second end or edge is provided with an attachment device 1411 for attachment to the other inner layer. The ratchet structure 1422 is arranged near the second end or edge of the inner layer 1445. The ratchet structure 1422 may have locking surfaces facing away from the primary actuator 1401*a*.

At the second end of the primary actuator 1401*a*, a gripping member 1406 having a secondary actuator 1401*b* may be arranged, which is to interact with the ratchet structure 1422. The gripping member 1406 may be attached at the second edge of the primary actuator 1401*a* and extend towards the first edge of the primary actuator 1401*a*. Furthermore, the gripping member may be bendable away from the primary actuator 1401*a* towards the ratchet structure, such as to form a protruding edge, which may engage a locking surface of the ratchet structure to lock the primary actuator 1401*a* relative to the ratchet structure 1422. The bending of the gripping member 1406 may be provided by a secondary actuator 1401*b*, which together with the gripping member 1406 may form a bi-layer structure.

Outside the gripping member, and connecting the outside of the primary actuator 1401*a* and the inner layer 1445 may be a cover structure 1442, which may also serve as a biasing member for biasing the gripping member towards the ratchet structure 1422.

Figure 19A:
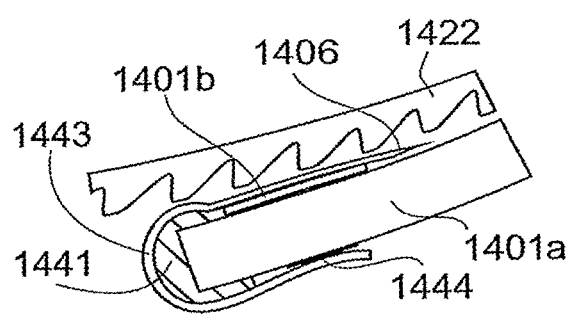
FIGS. 19a-19b schematically illustrate parts of the actuation unit according to a version of the fourteenth embodiment.
Figure 19B:
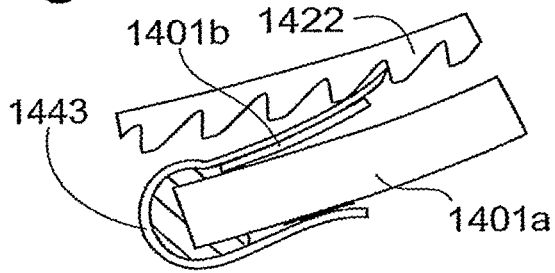

FIGS. 19*a*-19*b* illustrate a first design of the gripping member 1406, wherein a tip spring 1443 is arranged to enclose the edge of the primary actuator 1401*a*, possibly with a reinforcement structure 1441 provided between the edge and the tip spring 1443. The secondary actuator 1401b may be arranged on the inside of the gripping member so as to provide a bendable bi-layer structure.

Figure 20A:
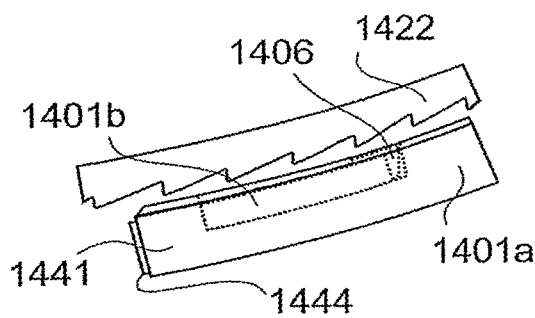
FIGS. 20a-20b schematically illustrate parts of the actuation unit according to another version of the fourteenth embodiment.
Figure 20B:
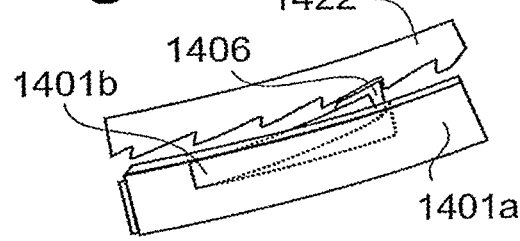

FIGS. 20a-20b illustrate a second design of the gripping member 1406, wherein the secondary actuator is provided at least partly in a recess in the primary actuator 1401a. The secondary actuator 1401b is made bendable, with one end of it attached to an end of the recess and the other end of it provided with a gripping member 1406.

In the configuration of FIGS. 20a, 20b the secondary actuator 1401b and the primary actuator 1401a may both be constructed from one monolithic piece of active material. This monolithic unit may have multiple electrode patterns for both the primary actuator and the secondary actuator. It is possible to route the signal wires for the secondary actuator along the internal layers of the primary actuator back to the base within the housing 1407. The gripping member 1406 may comprise an extra component that is bonded to the active material, and may include a wear resistant coating, or it may be an extension of the active material itself, but without electrodes and therefore inactivated. In addition, the reinforcement region 1441 can most simply be active material that is unelectroded, i.e. inactive. A simple bus bar 1444 can be used to connect the internal electrodes of the secondary actuator layers to the signal traces for the secondary actuator that may run through or along the primary actuator. This way, the entire structure can be manufactured in an automated way reducing assembly requirements. In addition, in this configuration, all of the actuator electrical connections can be made in the housing and all electrical traces can be sealed off from the environment.

In a configuration with primary actuators that can contract instead of expand, the cover structure 1442 will return the actuator to its original shape upon deactivation. In this sense, the gripping member advances along the compression member during the turn off phase of the actuation cycle and the compression level is increased during the activation phase of the actuation cycle. Such an actuation cycle will be observed in a memory alloy implementation of the embodiment.

This embodiment is suitable for polymer and shape memory materials. In particular it is very suitable for shape memory materials. The reason for this is that shape memory materials are very robust and can withstand the wear and tear of the surrounding environment, since they don't require electrolytes that can leak or have thin sensitive dielectric layers that can be punctured. Also the embodiment allows for rapid compression with the shape memory material during the heating cycle with a slower reset during the cooling cycle. Full advantage can be taken of impulse heating for the memory material, thereby achieving extremely rapid pressure onset rates (which is suitable for ECP or impulse DVT applications) and maximum stroke can be achieved per actuation cycle, given the long length of the primary actuators. Finally, the configuration can employ power down pressure maintenance so that power must only be provided to the active material during movements. In this way, the overall device efficiency in applications requiring significant high-pressure duty cycles can be maintained at a relatively high level, even with temperature activated memory materials or more inefficient polymer materials.

The actuation unit 1400 of FIGS. 18-20b may operate as follows.

First, the compression device is arranged around the body part, and the second edges of the inner layer 1445 are joined by the fasteners 1411, so that the compression device fits snuggly around the body part.

As an optional second step, the gripping member 1406 is caused to engage a portion of the ratchet structure 1422, which is at the part of the ratchet structure that is closest to the housing 1407.

Third, the primary actuator 1401a is activated so as to expand, thereby causing the gripping member 1406 to be displaced towards the end of the ratchet structure 1422, which is farthest away from the housing 1407.

As the primary actuator 1401a is expanded, the gripping member 1406 may be pushed over a ramp surface and into engagement with the next locking surface of the ratchet structure 1422. Alternatively, the secondary actuator 1401b may be used to disengage the gripping member from its engagement with the ratchet structure, and then to re-engage with the next locking surface.

Figure 21:
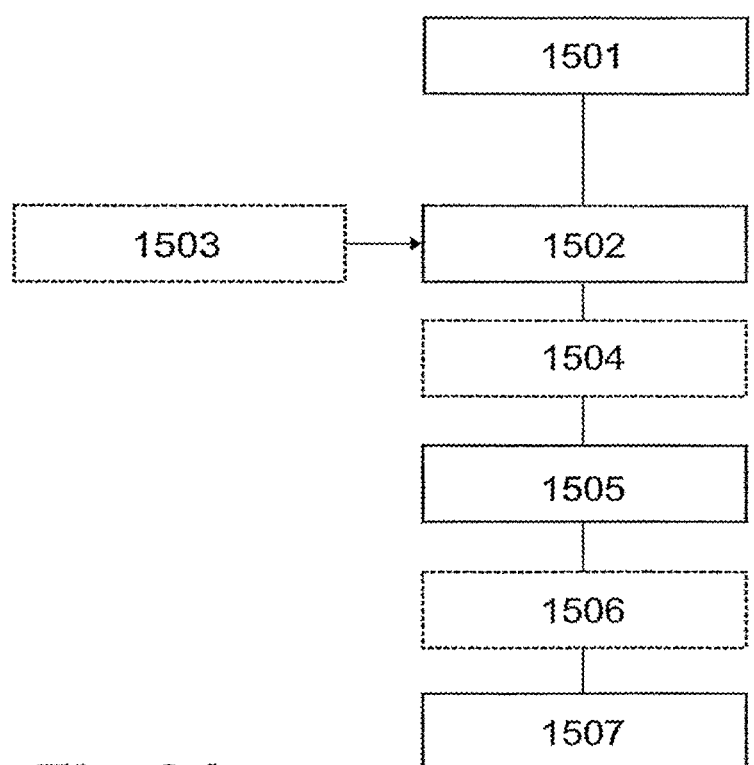
FIG. 21 is a block diagram, schematically illustrating component of the compression device.

FIG. 21 is a block diagram, schematically illustrating components of the compression device. According to the design strategy illustrated in FIG. 21, an active material actuator 1502, controlled by a controller 1501 may be arranged to interact with a compression member 1507 via a motion rectification device 1505. Optionally, a motion amplifying mechanism 1504 may be provided between the active material actuator 1503 and the motion rectification device 1505. Also optionally, a transmission mechanism 1506 may be provided, as in FIGS. 5a-5c, 8a-8b and 9, between the motion rectification device 1505 and the compression member 1507. Also optionally, a biasing element 1503 may be provided to bias the active material actuator 1502 towards the motion amplifying mechanism 1504, if any, or towards the motion rectification device 1505.

Figure 22:
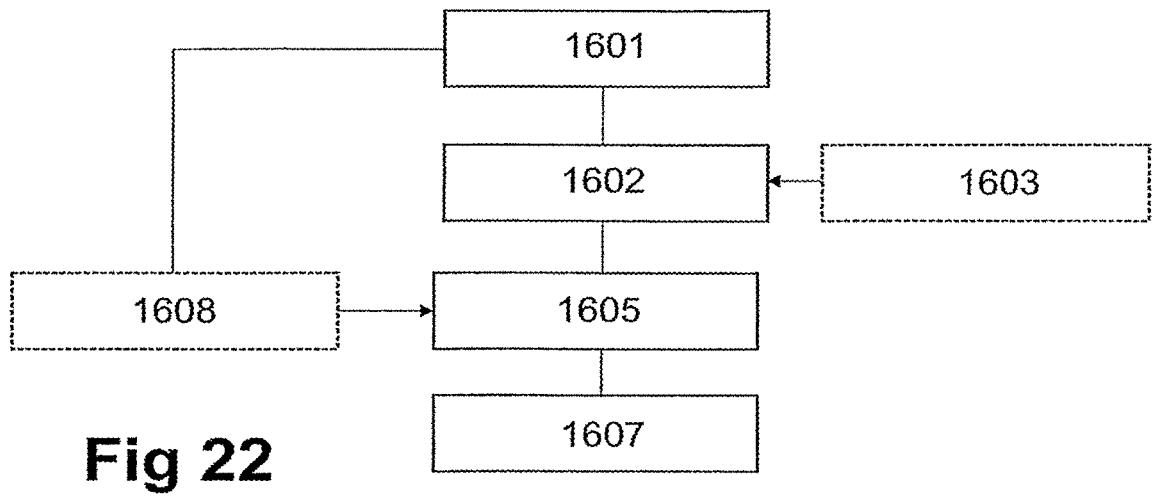
FIG. 22 is a block diagram, schematically illustrating components of the compression device according to another embodiment.

FIG. 22 is a block diagram, schematically illustrating components of the compression device according to another embodiment. According to the design strategy illustrated in FIG. 22, a primary actuator 1602, controlled by a controller 1601 may be arranged to interact with a compression member 1607 via a motion rectification device 1605. Optionally, an engagement/disengagement actuator 1608 may be provided for controlling the primary actuator's 1602 engagement with the motion rectification device 1605. The engagement/disengagement actuator 1608 may also be controlled by the controller 1601. Optionally, a biasing element 1603 may be provided to bias the active material actuator 1602 towards the rectification device 1605.

Figure 23:
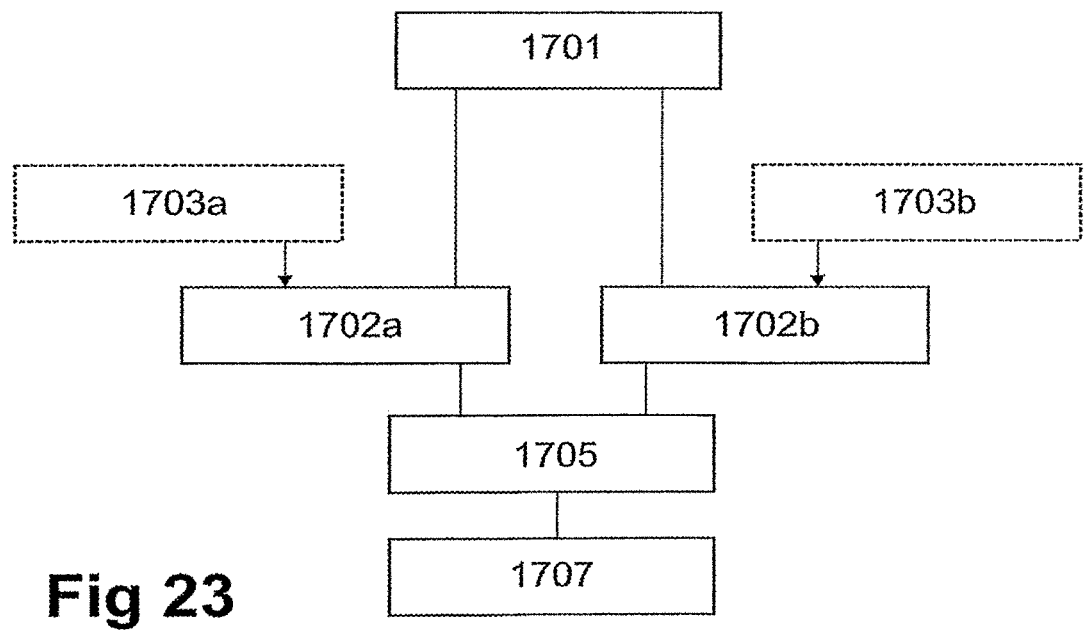
FIG. 23 is a block diagram, schematically illustrating components of the compression device according to yet another embodiment.

FIG. 23 is a block diagram, schematically illustrating components of the compression device according to yet another embodiment. In this design strategy, a controller 1701 controls two actuator sets 1702a, 1702b operating in parallel, and which may be provided with a respective biasing element 1703a, 1703b. The actuator sets 1702a, 1702b may engage a compression member 1707 via a motion rectification device 1705.

Figure 24A:
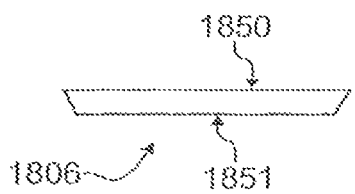
FIGS. 24a-24b schematically illustrate gripping member designs according to a first embodiment.
Figure 24B:
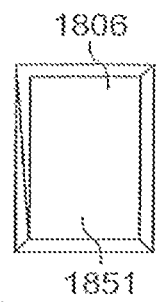

FIGS. 24a-24b schematically illustrate gripping member designs according to a first embodiment, wherein the gripping member 1806 tapers from the actuator facing side 1850 towards the movable member facing side 1851.

Figure 25A:
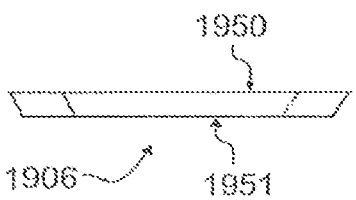
FIGS. 25a-25b schematically illustrate gripping member designs according to a second embodiment.
Figure 25B:
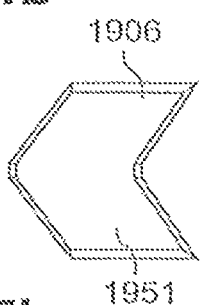
Figure 26A:
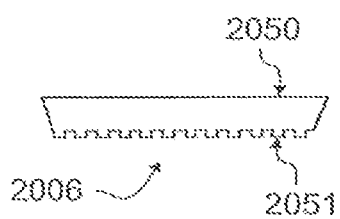
FIGS. 26a-26e schematically illustrate designs for gripping members and/or movable members according to a third embodiment.
Figure 26B:
Figure 26C:
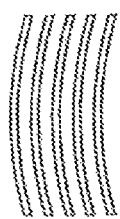
Figure 26D:
Figure 26E:
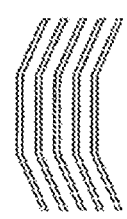
Figure 27A:
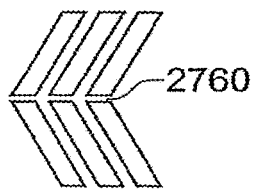
FIGS. 27a-27l schematically illustrate further designs for gripping members and/or movable members.
Figure 27B:
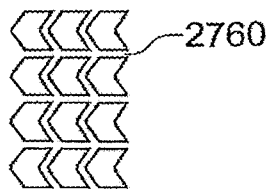
Figure 27C:
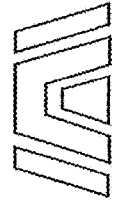
Figure 27D:
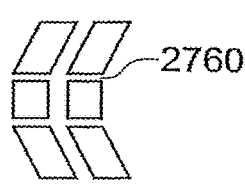
Figure 27E:
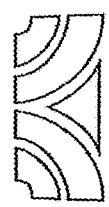
Figure 27F:
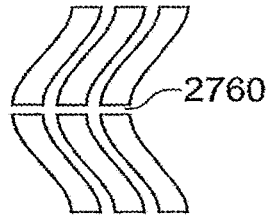
Figure 27G:
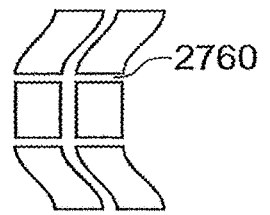
Figure 27H:
Figure 27I:
Figure 27J:
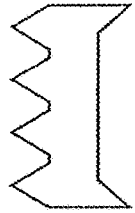
Figure 27K:
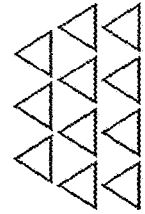
Figure 27L:
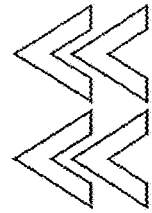
Figure 28A:
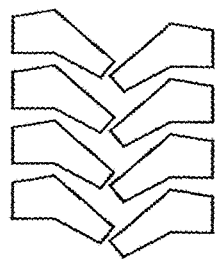
FIGS. 28a-28f schematically illustrate further designs for gripping members and/or movable members.
Figure 28B:
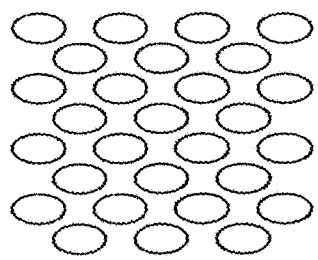
Figure 28C:
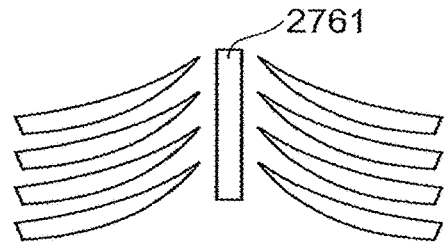
Figure 28D:
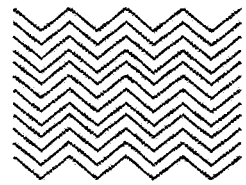
Figure 28E:
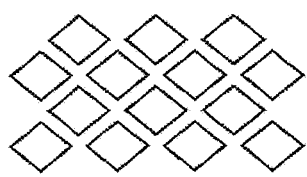
Figure 28F:
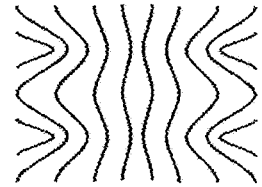

FIGS. 25a-25b schematically illustrate gripping member designs according to a second embodiment, wherein the gripping member tapers, just like in FIGS. 24a-24b, but wherein the gripping member is arrow-shaped. Such a tip may be oriented so that no edge can catch on the movable member, and also helps keep desirable forces on the movable member so that it stays straight during tightening.

FIGS. 26a-26e schematically illustrate gripping member designs according to a third embodiment, wherein the gripping member 2006 tapers from an actuator facing side 2050 towards the movable member facing side 2051, and wherein the latter side is microribbed according to any one of the patterns provided in FIGS. 26*b*-26*e*. From FIGS. 26*b*-26*e*, it is recognized that the gripping member designs indicated in FIGS. 24*a*-24*b* and 25*a*-25*b* may be combined with microribs, providing a ratchet structure on the gripping member. By providing asymmetric teeth on the ratchet structure, grip on the movable member may be further enhanced. V-shaping may facilitate removal of particles (dust, dander) from the ratchet structure, and may also provide acoustic dampening.

FIGS. 27*a*-27*l* schematically illustrate further gripping member designs, all of which being intended to move in a main direction from right to left vis-à-vis a movable member. The gripping member may be provided with an alignment through 2760 extending in the main direction, as is illustrated in FIGS. 27*a*, 27*b*, 27*d*, 27*f*, 27*g* and 27*l*. Such alignment troughs 2760 may be used to control the direction of movement of the movable member, to avoid deviations, and may be provided on the gripping member and/or on the movable member. Basically, any interacting alignment structures may be provided on the gripping member and on the movable member (whether a wheel or a strap) for ensuring that the relative movement between the gripping member and the movable member follows an intended direction.

Alignment troughs 2760 can be used in conjunction with matching structures on the compression member or movable member surface to maintain alignment during the compression cycle. Alternatively such designs can be patterned onto the compression member or movable member surface so as to interact in an advantageous way with the gripping member surface. Matching patterns on both the gripping member and the compression member can be used to enhance force capabilities of the interface (through positive locking of the two surfaces), maintain alignment during each stroke, keep the compression member centered with respect to the actuation unit, etc.

Embossed alignment members 2761 can be used in conjunction with matching structures on the gripping member surface to maintain alignment during the compression cycle.

FIGS. 28*a*-28*f* schematically illustrate further alternative gripping member designs.

Whereas the actuators have been described for use with a compression member in a compression treatment device, such actuators may have further areas of application, such as for seatbelt tightening, high force cable drives, cable winding mechanisms, continuos sheet processing equipment, adjustable belt drive tightening systems, adjustable flow restrictors, peristaltic pumps, etc.

It is noted that in embodiments where locking surfaces (FIGS. 10*a*-10*d*, 13*a*-13*c*, 16, 18, 19*a*-19*b*, 20*a*-20*b*, occur, the spacing between two adjacent locking surfaces may be less than the maximum available stroke length of the actuator. In some embodiments, the spacing of the locking surfaces may be set at a fraction of the available stroke length of the actuator, such that under low force conditions (little compression) the actuator can step over a plurality of locking surfaces with each stroke, but as the compression member tightens around the body part (increased compression levels) and the actuator steps become smaller (due to the increased force from the compression member), the resulting spacing of the locking surfaces is still sufficient that at least single steps can be made with each complete actuator stroke. Thereby one means of limiting the force capabilities of this configuration is by design of the ratio between the locking surface spacing and the available actuator stroke length. When the force requirement exceeds the capability for the actuator to take at least a single step, the rectification will be lost and the compression member will no longer be able to further advance.

It is recognized that the actuators disclosed herein may be used in any application wherein a strap is to be tightened around an object or for pulling a strap. Hence, the disclosure herein is not limited to devices for compressive treatment of body parts, but to any device for tightening or pulling a strap.

The invention claimed is:

1. A device for compressive treatment of a body part of a user, the device comprising:
   an actuator layer sized and adapted to form a sleeve around the body part, the actuator layer comprising:
     a plurality of compression members dimensioned to at least partly encircle the body part;
     a plurality of connection members, at least one connection member of the plurality of connection members connected to each of the plurality of compression members; and
     a plurality of actuation units cooperating with the plurality of compression members to tighten the compression members and provide a compressive force to the body part when in use, wherein each actuation unit comprises:
       a housing,
       a spindle provided at least partially in the housing, wherein at least one connection member of the plurality of connection members is windable onto the spindle, and
       a motor operatively connected to the spindle such that the at least one connection member is windable onto the spindle to tighten the corresponding compression member and provide a compressive force to the body part; and
   a control unit operably coupled to the plurality of actuation units to provide compressive lymphedema treatment to the body part of the user using the plurality of compression members.

2. The device of claim 1, wherein each of the plurality of compression members is connected to a single connection member of the plurality of connection members.

3. The device of claim 1, wherein each of at least two connection members of the plurality of connection members is coupled to portions of a single compression member of the plurality of compression members.

4. The device of claim 1, wherein at least one of at least two connection members of the plurality of connection members is windable onto the spindle, wherein each of the at least two connection members extend from the spindle.

5. The device of claim 4, wherein each of the at least two connection members extend in different directions from the spindle and are windable onto the spindle.

6. The device of claim 1, wherein at least one part of each connection member of the plurality of connection members is attached to a corresponding compression member of the plurality of compression members and another part of each connection member of the plurality of connection members interacts with a corresponding actuation unit of the plurality of actuation units.

7. The device of claim 1, wherein the plurality of connection members and the plurality of actuation units are reusable and the plurality of compression members are disposable.

8. The device of claim 1, wherein the device comprises one or more sensors, wherein the one or more sensors are arranged to provide a feedback signal from the one or more sensors to the control unit representative of at least the compressive force being provided to the body part, wherein the control unit is configured to provide a control signal to the plurality of actuation based at least on the feedback signal.

9. The device of claim 8, wherein the control unit and the one or more sensors are at least partially integrated with the device.

10. The device of claim 1, wherein the spindle of each of the plurality of actuation units is rotatably arranged about a substantially central axis of each corresponding actuation unit.

11. The device of claim 10, wherein the motor of each of the plurality of actuation units comprises a rotary motor, the rotary motor comprising a rotatable output part coaxial with each corresponding spindle.

12. The device of claim 10, wherein the motor of each of the plurality of actuation units is connected to each corresponding spindle using a power transmission mechanism.

13. The device of claim 1, wherein each compression member of the plurality of compression members comprises at least one or more passive materials.

14. The device of claim 1, wherein the motor of each of the plurality of actuation units is operatively connected to each corresponding spindle such that each corresponding at least one connection member is windable off of each corresponding spindle.

15. A system for compressive treatment of a body part of a user, the system comprising:
    a sleeve positionable around the body part, the sleeve comprising a plurality of compression devices, each compression device comprising:
        a compression member dimensioned to at least partly encircle the body part;
        at least one connection member coupled to the compression member; and
        an actuation unit cooperating with the compression member to tighten the compression member and provide a compressive force to the body part when in use, wherein the actuation unit comprises:
            a housing,
            a spindle provided at least partially in the housing, wherein the at least one connection member is windable onto the spindle,
            a motor operatively connected to the spindle such that the at least one connection member is windable onto the spindle, wherein the actuation unit is arranged to tighten the compression member by pulling portions of the compression member in opposite directions using the at least one connection member; and
    a control unit operably coupled to the actuation unit of each of the plurality of compression devices to provide compressive lymphedema treatment to the body part of the user using the sleeve.

16. The system of claim 15, wherein the system comprises one or more sensors, wherein the one or more sensors are arranged to provide a feedback signal from the one or more sensors to the control unit representative of at least the compressive force being provided to the body part, wherein the control unit is configured to provide a control signal to the actuation unit of each of the plurality of compression devices based at least on the feedback signal.

17. The system of claim 15, wherein the motor of each actuation unit is operatively connected to each corresponding spindle such that each corresponding at least one connection member is windable onto each corresponding spindle to tighten each corresponding compression member and provide a compressive force to the body part and such that each corresponding at least one connection member is windable off of each corresponding spindle.

* * * * *

UNITED STATES PATENT AND TRADEMARK OFFICE
CERTIFICATE OF CORRECTION

PATENT NO. : 10,828,220 B2  
APPLICATION NO. : 15/008917  
DATED : November 10, 2020  
INVENTOR(S) : Landy Toth Page 1 of 1

It is certified that error appears in the above-identified patent and that said Letters Patent is hereby corrected as shown below:

On the Title Page

Item (73) Assignee, please remove:  
'Tactile Systems Technology Inc.,  
Minneapolis, MN (US)'

And replace it with:  
--Swelling Solutions, Inc.,  
Minneapolis, MN (US)--

Signed and Sealed this  
Eighth Day of March, 2022

Drew Hirshfeld  
*Performing the Functions and Duties of the*  
*Under Secretary of Commerce for Intellectual Property and*  
*Director of the United States Patent and Trademark Office*